US009816926B2

(12) United States Patent
Jin et al.

(10) Patent No.: US 9,816,926 B2
(45) Date of Patent: Nov. 14, 2017

(54) MULTIPLEX SUSPENSION ASSAY/ARRAY USING LIFETIME CODING

(71) Applicant: Macquarie University, New South Wales (AU)

(72) Inventors: Dayong Jin, New South Wales (AU); Yiqing Lu, New South Wales (AU); Jiangbo Zhao, New South Wales (AU)

(73) Assignee: MACQUARIE UNIVERSITY, New South Wales (AU)

( * ) Notice: Subject to any disclaimer, the term of this patent is extended or adjusted under 35 U.S.C. 154(b) by 0 days.

(21) Appl. No.: 14/410,015

(22) PCT Filed: Jun. 21, 2013

(86) PCT No.: PCT/AU2013/000672
§ 371 (c)(1),
(2) Date: Dec. 19, 2014

(87) PCT Pub. No.: WO2013/188927
PCT Pub. Date: Dec. 27, 2013

(65) Prior Publication Data
US 2015/0185149 A1    Jul. 2, 2015

(30) Foreign Application Priority Data

Jun. 22, 2012 (AU) ................................ 2012902652

(51) Int. Cl.
*G01N 21/64* (2006.01)
*C40B 70/00* (2006.01)
(Continued)

(52) U.S. Cl.
CPC ....... *G01N 21/6408* (2013.01); *B42D 25/382* (2014.10); *B42D 25/387* (2014.10);
(Continued)

(58) Field of Classification Search
CPC ...................... G01N 21/6408; G01N 21/6428
See application file for complete search history.

(56) References Cited

U.S. PATENT DOCUMENTS

| 5,626,134 A | 5/1997 | Zuckerman |
| 8,134,705 B2 * | 3/2012 | Kaduchak .......... G01N 15/1404 356/337 |

(Continued)

FOREIGN PATENT DOCUMENTS

| CN | 101735216 | 6/2010 |
| WO | WO96/00901 | 1/1996 |

(Continued)

OTHER PUBLICATIONS

Wang et al., Luminescence Tuning of Upconversion Nanocrystals, Mar. 22, 2010, Chemistry European Journal, vol. 16, pp. 4923-4931.*

(Continued)

*Primary Examiner* — Christine Sung
(74) *Attorney, Agent, or Firm* — Seed IP Law Group LLP

(57) ABSTRACT

A system, device and/or method for multiplex assays. In a particular, but non-limiting, example there is provided a multiplex array, such as a suspension array. Luminescence decay lifetimes are utilized for probes in a suspension array, and coding/decoding the codes from time-resolved spectra. Lifetime populations can be generated at distinct color bands. A novel temporal technique or dimension is applied over conventional spectral and intensity combinations, thereby expanding the multiplexing capacity of a suspension array. In one example form, the multiplexing capacity of a suspension array can be expanded to the order of about $5^8$. This provides a reliable, high-throughput and relatively inexpensive solution for multiplex assays in various areas of application such as life sciences, data storage and security.

19 Claims, 13 Drawing Sheets

(51) Int. Cl.
  C09K 11/02      (2006.01)
  C09K 11/06      (2006.01)
  C09D 11/50      (2014.01)
  C09K 11/77      (2006.01)
  B42D 25/382     (2014.01)
  B42D 25/387     (2014.01)
  G01N 33/542     (2006.01)
  G01N 33/58      (2006.01)

(52) U.S. Cl.
  CPC .............. *C09D 11/50* (2013.01); *C09K 11/02* (2013.01); *C09K 11/025* (2013.01); *C09K 11/06* (2013.01); *C09K 11/7773* (2013.01); *C40B 70/00* (2013.01); *G01N 21/6428* (2013.01); *G01N 33/542* (2013.01); *G01N 33/582* (2013.01); *C09K 2211/182* (2013.01)

(56) References Cited

U.S. PATENT DOCUMENTS

| | | | |
|---|---|---|---|
| 2001/0046673 | A1 | 11/2001 | French et al. |
| 2007/0274909 | A1* | 11/2007 | Justel ............... A61K 41/00 424/1.53 |
| 2008/0207466 | A1 | 8/2008 | Mozdy et al. |
| 2009/0314946 | A1 | 12/2009 | Song et al. |
| 2011/0269151 | A1 | 11/2011 | Kim |

FOREIGN PATENT DOCUMENTS

| | | |
|---|---|---|
| WO | WO98/15830 | 4/1998 |
| WO | WO01/98765 | 12/2001 |
| WO | WO03/035671 | 5/2003 |
| WO | WO2006/098923 | 9/2006 |
| WO | WO2008/104637 | 9/2008 |
| WO | WO2011/087916 | 7/2011 |

OTHER PUBLICATIONS

Wang et al., Tuning Upconversion through energy migration in core-shell nanoparticles, Oct. 23, 2011, Nature Materials, vol. 10, pp. 968-973.*

"Microsphere sedimentation arrays for multiplexed bioanalytics", Christoph Moser, Torsten Mayr, and Ingo Klimant; Analytica Chimica Acta 558, 2006, pp. 102-109.

"Luminescence decay time encoding of magnetic micro spheres for multiplexed analysis", Torsten Mayr, Christoph Moser, and Ingo Klimant; Analytica Chimica Acta 597, 2007, pp. 137-144.

"Encoded Microcarriers for High-Throughput Multiplexed Detection", Robert Wilson, Andrew R. Cossins and David G. Spiller; Angew, Chem. Int. Ed., 2006, col. 45, pp. 6104-6117.

"Lanthanide-encoded polystyrene microspheres for mass cytometry-based bioassays"; Ahmed I. Abdelrahman; Copyright 2011.

* cited by examiner

MULTIPLEX SUSPENSION ASSAY/ARRAY USING LIFETIME CODING

CROSS-REFERENCE TO RELATED APPLICATIONS

This application claims priority to International Application No. PCT/AU2013/000672, filed Jun. 21, 2013, which claims priority to Australian Patent Application No. 2012902652, filed Jun. 22, 2012, each of which is incorporated by reference in its entirety.

TECHNICAL FIELD

The present invention generally relate's to multiplex assays and/or arrays, and more particularly in one example to suspension based assays and/or arrays In other forms the present invention provides a method, system and/or device for application in the example fields of biotechnology and life sciences, such as in the identification and quantification of biomolecule species, and in security such as in security inks or printing.

BACKGROUND

The frontiers of molecular biology have necessitated high-throughput analytical technologies, capable of simultaneous identification and quantification of large numbers of biomolecule species. This covers the broad bioinformatics area of genomics, proteomics, intercellular and molecular signalling, metabolomics, cytomics and personalized medicine. For example, due to large variations of individuals' genetic signatures and frequent failures of traditional symptom-diagnostics, the emerging field of personalized medicine seeks to detect personal gene expression profiles, in order to focus upon therapies that are specific for each individual. Wider applicability of such personalized biomolecular diagnostics is currently hindered by issues such as assay speed and cost, as well as the complexity of the genome/proteome. An ideal tool would be a library or database of analytical channels, capable of supporting the analysis of not tens, but thousands of distinctive molecular targets.

In data storage, the main goal of multiplexing is to increase the data storage capacity within spatially-limited memory elements. In security printing of banknotes, identity cards, trademark tags, etc., multiplexing helps to prevents forgery, tampering or counterfeiting, and thermochromatic, magnetic, multi-colour fluorescent, and optically variable colour-changing inks have been used for this purpose. Multiplexing typically requires a matrix of optical codes, ideally carried by nano-/micro-sized objects, each of which should be accurately identifiable at high-speed and preferably in a low-cost fashion.

In principle, planar array biochips, used in multiplex assay techniques, provide infinite multiplexing capacity based on predetermined positions of microspots in the planar array. However in practice, this technology fails to provide sufficiently accurate quantitative data. For example, due to its requirement for high-precision robot encoding, diffusion concerns and/or varied biological environments between each reaction microspot. Moreover, relatively high manufacturing cost and a requirement that array plates be manufactured in fixed formats prior to analysis, interferes with or inhibits useful customisation.

Suspension arrays are emerging as a future leading technology for use in multiplex assay based molecular detection. Suspension arrays are based on ensembles of microspheres that are specially coded, most frequently by varying combinations of fluorescent dyes. The microspheres are thus endowed with a range of individually identifiable colour codes individually assigned to a specific analyte. Major advantages of suspension arrays include rapid reaction kinetics, the absence of washing leading to higher sample throughput, as well as reproducible manufacture of microsphere families. Suspension arrays are also providing potential for quantitative assays due to the uniform surface of microcarriers, simplicity of use and decreased expense compared to alternatives.

The level of spectral multiplexing available using suspension arrays is currently limited to around 100, achieved by encoding the microspheres with fluorescent dyes at varying intensity ratios. Producing a larger number of codes by using colours and intensities is difficult, due to the broad spectral width of fluorescent dyes and background fluorescence in the most popular microsphere material, polystyrene. Alternative methods include using differently sized and shaped microspheres, patterned reflective metal nanorods, micromachined signatures, spatially selective photobleached microspheres, rare-earth mass cytometry, and rare-earth doped glass microbarcodes. These approaches are considered unlikely to become mainstream due to various deficiencies (e.g. large size and/or high density materials).

Graphical encoding, for example designing particles as 1D barcodes, 2D or even 3D patterns, offers multiplexing capacity competitive to planar arrays. But the deciphering of graphic codes requires an active orientation mechanism and high-resolution pattern recognition, fundamentally restricting the analytical throughput. Electronic encoding can also generate numerous codes, but a primary weakness stems from a requirement for large dimensions (>100 µm). Other techniques, including spectrometric encoding making use of Raman scattering, IR absorption or mass spectroscopy fingerprints and physical encoding utilizing size, shape, and magnetism, are also of limited use due to respective limitations.

Optical encoding on the basis of digitized intensities at different fluorescence colour bands, is considered the most practical method. However, spectral overlapping of fluorescent probes becomes problematic when more than about ten intensities are desired, despite attempts to replace conventional organic dyes with novel materials such as quantum-dots. The multiplexing capacity of optical encoding remains practically limited to about $10^2$. Decoding such a large number of codes presents another challenge. Although imaging-based decoding systems can, in principle, decode any suspension array, slight variations in the height of some particles on a planar surface will seriously interfere with an intensity-based decoding process.

Thus, there are outstanding problems to overcome or ameliorate so as to provide new or improved multiplex assays and/or arrays, for example to be able to increase the number of coding dimensions, in which the surface quantitative binding assays are immune to these codes. These codes should be able to be resolved under high-throughput conditions.

The reference in this specification to any prior publication (or information derived from the prior publication), or to any matter which is known, is not, and should not be taken as an acknowledgment or admission or any form of suggestion that the prior publication (or information derived from the prior publication) or known matter forms part of the common general knowledge in the field of endeavour to which this specification relates.

SUMMARY

This Summary is provided to introduce a selection of concepts in a simplified form that are further described below in the Preferred Embodiments. This Summary is not intended to identify key features or essential features of the claimed subject matter, nor is it intended to be used to limit the scope of the claimed subject matter.

In various forms there is provided a system, device and/or method for multiplex assays. In a particular, but non-limiting, example there is provided a multiplex array, such as a suspension array.

Suspension arrays, as an alternative form to planar arrays with general clinical potential, suffered from inferior capacity practically limited to about $10^2$ codes. The Applicant has developed a new multiplex array, which in a preferred example provides a means to encode suspension arrays by utilising and/or engineering luminescence decay lifetimes of probes, and decoding the codes produced, obtained or generated from time-resolved spectra. In one example form, lifetime populations can be generated at distinct colour bands, for example via multiple mechanisms applied on different probes.

A novel temporal based technique or dimension is applied, or applied over or in conjunction with conventional spectral and intensity combinations, thereby expanding the multiplexing capacity of a multiplex array, such as a suspension array. In one example form, the multiplexing capacity of conventional suspension arrays may be expanded to the order of about $10^6$. Typically, conventional spectral codes can generate autofluorescence background for the beads' surface bioassays, affecting both sensitivity and quantification performance.

The Applicant has realized the potential of using lifetime, being a direct parameter associated with fluorescence, so that lifetime can be exploited to generate a new dimension of optical identities, in addition to spectrum and intensity, for multiplexed detection towards high-throughput screening. Particularly, luminescence probes provide a much larger field of play for the lifetime dimension, as well as a background-free advantage, so that control and differentiation of lifetimes provide a practical and accurate alternative compared to conventional known methods.

The Applicant has developed, in example forms, rare-earth luminescence based optical codes and/or probes, which are dark under visible light illumination, and a background-free or background-reduced substrate, such as a bead substrate, for sensitive and quantitative surface molecular bioassays. This, and other example forms, provide a reliable, high-throughput and relatively inexpensive solution for multiplex assays, opening up numerous opportunities or applications in, for example, life science and biological applications including genomics, proteomics, pharmacology, diagnostics, etc., security applications including security inks or printing of banknotes, identity cards, trademark tags, etc., and data storage applications.

In one aspect there is provided a multiplex assay method for identifying a luminescent probe in a multiplex array, the method comprising: stimulating the luminescent probe to produce luminescence; and measuring the decay lifetime of the luminescence resulting from the stimulation.

In another aspect there is provided a multiplex assay system for detection of an analyte, the system comprising: a luminescent probe configured to bind the analyte; a stimulator for exciting the luminescent probe to produce luminescence; and a detector for measuring the decay lifetime of the luminescence resulting from the excitation.

In another aspect there is provided a luminescent probe for use in a multiplex array, the luminescent probe including a rare earth element capable of being stimulated to produce luminescence, thereby enabling a decay lifetime of the luminescence resulting from the stimulation to be measured.

Preferably, the multiplex array is a suspension array.

In one example the method further includes: stimulating a plurality of luminescent probes to produce luminescence; measuring the decay lifetimes of the luminescence; and, time-resolving the luminescence to identify a type of luminescent probe.

In another example form, the time-resolved luminescence provides lifetime populations of different types of luminescent probe. In another example form, the decay lifetimes are microsecond decay lifetimes. In another example form, the time-resolved luminescence provides one or more codes. In another example form, the time-resolved luminescence are generated at distinct colour bands. In another example form, the distinct colour bands are used to provide a library of time-domain based optical identities. In another example form, stimulating the probe includes exposing the probe to electromagnetic radiation.

In another example form, the luminescent probe is stimulated by UV radiation. In another example form, the luminescent probe is stimulated by IR radiation. In another example form, the luminescent probe remains dark for visible light excitation. In another example form, the luminescent probe is part of a microsphere. In another example form, the probe includes one or more rare earth element. In another example form, the probe includes one or more lanthanide.

In another example form, the decay lifetime of the luminescent probe has been altered using Luminescence Resonance Energy Transfer (LRET). In another example form, two or more probes having distinguishable decay lifetimes are previously tuned using LRET.

In another example form, the luminescent probe includes one or more nanocrystals. In another example form, the decay lifetime of the luminescent probe has been altered by altering the nanocrystals. In another example form, the decay lifetime of the luminescent probe has been altered by adjusting a doping concentration of the nanocrystals. In another example form, the nanocrystals are rare-earth doped upconversion nanocrystals. In another example form, the decay lifetime is varied by altering a donor-to-acceptor distance. In another example form, the donor-to-acceptor distance is altered by changing respective concentrations of donor and acceptor. In another example form, the decay lifetime of the luminescent probe has been altered by adjusting a differential concentration of a sensitizer-activator. In another example form, the nanocrystals are doped with ytterbium sensitizers and erbium or thulium emitters. In another example form, the nanocrystals are encapsulated into microspheres. In another example form, the decay lifetime of the luminescent probe has been altered by adjusting the size of the nanocrystals. In another example form, the decay lifetime of the luminescent probe has been altered by adjusting the crystal phase of the nanocrystals. In another example form, in a single colour band, there are more than ten nanocrystal populations having distinct decay lifetimes.

In another example form, the decay lifetimes are between 25.6 µs and 662.4 µs. In another example form, the decay lifetime of the luminescent probe has been altered by adding quencher dyes. In another example form, the decay lifetime of the luminescent probe has been altered by using a metal matrix within the probe to tune the decay lifetime. In another example form, the luminescent probe includes different lanthanide complex chelates or different host crystal structures. In another example form, measuring the decay lifetime of the luminescence is in addition to measuring the luminescence spectrum and luminescence intensity.

In other example forms, the probe is selected from the group of microspheres, nanoparticles or nanocrystals assembled to provide microspheres, rare-earth doped silica microspheres, microspheres embedding palladium (Pd) and/or platinum (Pt) phosphorescence, microspheres embedding charge-transfer (CT) excited transition emitters, and microspheres embedding charge-transfer (CT) excited transition emitters of ruthenium, osmium or rhenium.

In another example form, there are provided at least five distinct decay lifetimes in a red colour band. In another example form, there are provided at least five distinct decay lifetimes in a blue colour band. In another example form, there are provided at least four distinct decay lifetimes in a green colour band. In another example form, for a UV pulsed excitation beam and a IR pulsed excitation beam, the probe is resolved into four channels using band-pass colour filters, each channel having an initial intensity parameter and a decay lifetime parameter, thereby providing eight dimensions.

In other example forms, the probe is a nano- or micro-tag, sphere, particle or carrier. In other example forms, the probe includes an element selected from the group of Lanthanum, Cerium, Praseodymium, Neodymium, Promethium, Samarium, Europium, Gadolinium, Terbium, Dysprosium, Holmium, Erbium, Thulium, Ytterbium, Lutetium, Scandium and Yttrium.

BRIEF DESCRIPTION OF FIGURES

Example embodiments should become apparent from the following description, which is given by way of example only, of at least one preferred but non-limiting embodiment, described in connection with the accompanying figures.

PREFERRED EMBODIMENTS

Figure 1:
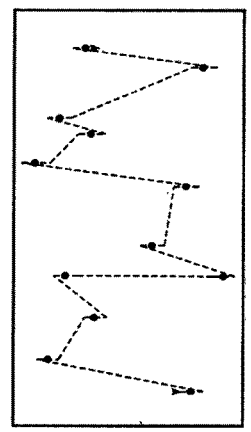
FIG. 1 illustrates an example decoding concept of time-resolved suspension arrays.
Figure 1:
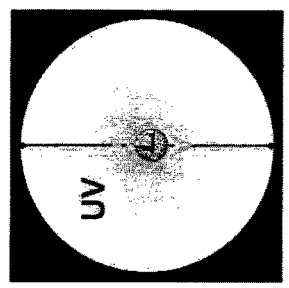
Figure 1:
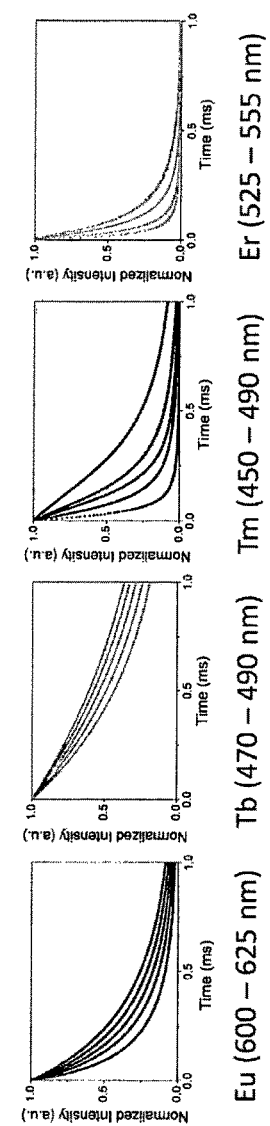
Figure 1:
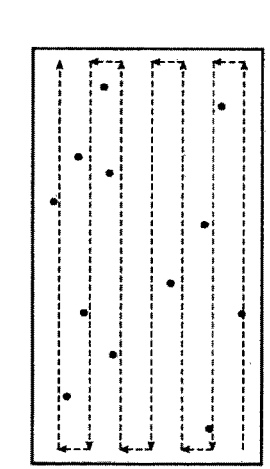
Figure 1:
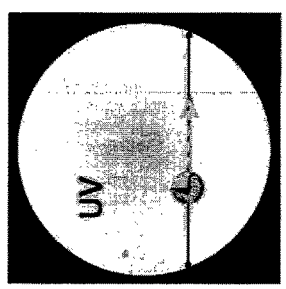
Figure 1:
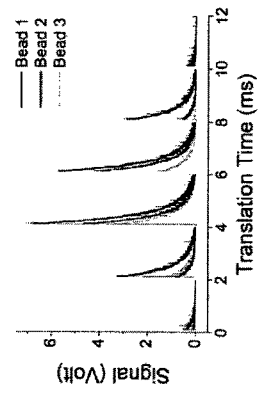

The following modes, given by way of example only, are described in order to provide a more precise understanding of the subject matter of a preferred embodiment or embodiments.

Time-Resolved Scanning: Multiplexed Detection in the Temporal Domain

The Applicant has extended the capability of multiplex assays, for example multiplexing in suspension arrays. This is achieved by utilising or adding a new temporal dimension. In one example, a possible factor of about 100 further codes has been achieved, based upon lifetimes, to the number of codes currently possible in spectral multiplexing, thus bringing the total possible multiplexing level to about 10,000 or more codes. This brings the multiplexing capability in line with the actual level of complexity in biological samples, and also allows a library or database of probes, such as specific microspheres, carrying about 10,000 codes to be built or produced, so as to give users far greater scope and more flexibility with multiplex assay design.

The rationale of the multiplexing strategy is based on the exploration of the temporal domain as an extra dimension in addition to spectrum and intensity. In one example one or more lanthanides were selected as example luminescent probes to produce time-resolved suspension arrays. Lanthanides have an extensive dynamic range associated with their exceptionally-long lifetimes (>100 μs), as well as other attractive properties including narrow emission spectra and large Stokes shift. Example embodiments can use any of the lanthanides, including Lanthanum, Cerium, Praseodymium, Neodymium, Promethium, Samarium, Europium, Gadolinium, Terbium, Dysprosium, Holmium, Erbium, Thulium, Ytterbium, and Lutetium, either individually or in any combination. Other example embodiments can use any of the rare earth elements, which include any of the fifteen lanthanides in addition to Scandium and Yttrium, either individually or in any combination.

The Applicant has identified a number of practical techniques, methods or mechanisms to precisely or accurately tune micro- and/or milli-second luminescent decay rates and produce individual probes and/or microspheres. In one non-limiting example, the probes/microspheres are rare-earth doped probes/microspheres. In another non-limiting example, the probes/microspheres are lanthanide doped probes/microspheres. In another non-limiting example, the probes/microspheres are rare-earth doped polystyrene probes/microspheres.

It will be appreciated that a variety of other types of probes/microspheres are possible, including, for example, nanoparticles assembled to provide microspheres, rare-earth doped silica microspheres, microspheres embedding palladium (Pd) and/or platinum (Pt) phosphorescence, and microspheres embedding charge-transfer (CT) excited transition emitters (such as ruthenium, osmium, and rhenium).

Multiplexed detection of two or more targets, for example five types of example microspheres are discussed, having clearly distinguishable lifetimes, purposely tuned via Luminescence Resonance Energy Transfer (LRET), have been demonstrated and successfully applied to various applications, for example simultaneous probing of different DNA strands.

Luminescent probes showing exceptionally long lifetimes (microseconds to milliseconds) provide advantages over organic fluorophores (of nanoseconds lifetime) in a plurality of fluorescence-based analytical techniques, including background-free biosensing and bioimaging, security application scanning or printing, high-accuracy Energy Transfer measurement, and low-power optical super-resolution imaging. The results allow a new optical library to be built carrying lifetime identifies on top of the overcrowded spectra dimension, in an effort to stimulate new discoveries in life sciences or other areas, such as security inks or dyes, which demand advanced analytical methods.

The decay lifetime of fluorescence, e.g. from organic dyes or quantum dots, is normally in the range up to tens of nanoseconds; however, materials containing certain families of elements, particularly the lanthanide metals or the platinum group metals, usually exhibit extended luminescence decays with lifetimes from microseconds to even milliseconds. Substituting long-lived probes for organic dyes as the donor of resonance energy transfer offers greater accuracy, a larger measurable range and higher labeling tolerance when measuring the distance between donor and accepter from the luminescence lifetime. Long lifetimes can also help lower the power requirement for stimulated emission depletion (STED) super-resolution imaging, for example enabling live monitoring without damaging biological samples or other physical samples such as for security authentication.

Moreover, the lifetime dimension has enormous potential for advanced high-throughput analytical techniques necessitated in modern security applications, microbiology, biochemistry and biomedicine. In a biological application, to simultaneously screen multiple biomolecular species, known as multiplexing, known prevalent techniques rely on a number of different bioprobes fluorescing distinguishable colours, which however blend with one another because their emission spectra typically have spillover issues. This crosstalk problem becomes aggravated as the number of bioprobes increase. For example, current state-of-the-art polychromatic flow cytometry allows measurement up to seventeen fluorescent colours (eleven from organic dyes and six from quantum dots) if only sophisticated colour compensation is provided, not to mention the equipment of four lasers and seventeen individual photodetectors as well as unsustainable cascading of dichroic mirrors and bandpass filters. As alternative approaches, other spectroscopic features, such as mass spectra or Raman spectra using special bioprobes, have been utilized in order to increase the multiplexing capacity. However, these methods are generally incompatible with fluorescence measurement, which otherwise gives an ultimate sensitivity usually two orders of magnitude higher.

In contrast, the Applicant has realized the potential of using lifetime, being a direct parameter associated with fluorescence, so that lifetime can be exploited to generate a new dimension of optical identities, in addition to spectrum and intensity, for multiplexed detection towards high-throughput screening. Particularly, luminescence probes provide a much larger field of play for the lifetime dimension, as well as a background-free advantage, so that control and differentiation of lifetimes provide a practical and accurate alternative compared to conventional known methods.

The discrimination of long luminescence lifetimes is generally beyond the capability of most known commercially available systems. The extraction of lifetime parameters has primarily been carried out in solution/suspension with assistance of post-processing, rather than on individual probes or micro-targets in real-time. This is not only simply owing to the unsuitable excitation/emission wavelength combination for luminescent probes, but also for three more fundamental reasons: 1) the extended luminescence decays may lead to unacceptably long processing time based on prevalent nonlinear fitting algorithms; 2) for cases of rapid lifetime measurement, which relies on low levels of luminescence signal, improper configuration of the detection channels may essentially prevent precise measurement for exceptionally-long lifetimes; 3) the noise of dark current or dark counts, which has been typically ignored for measuring lifetimes in the nanosecond range, have to be taken into account, since the signal profiles associated with long lifetimes incorporate a higher level of noise (proportional to the length of the detection window) that affect the accuracy in the results.

Luminescence Resonance Energy Transfer (LRET) for Tuning Luminescent Decay Rates A first technique, method or mechanism to precisely or accurately tune micro- and/or milli-second luminescent decay rates is based on Luminescence Resonance Energy Transfer (LRET), in which donors of a lanthanide complex, for example an europium complex, and energy acceptors, such as hexafluorophosphate salt, are in close proximity and interact with one another, and as a result, originally short lifetime acceptor dyes reduce long lifetime luminescence. Varying the donor-to-acceptor distance by changing their respective concentrations makes it possible to fine tune the luminescence lifetimes of both donor and acceptor, which is accompanied by an intensity change.

Figure 2:
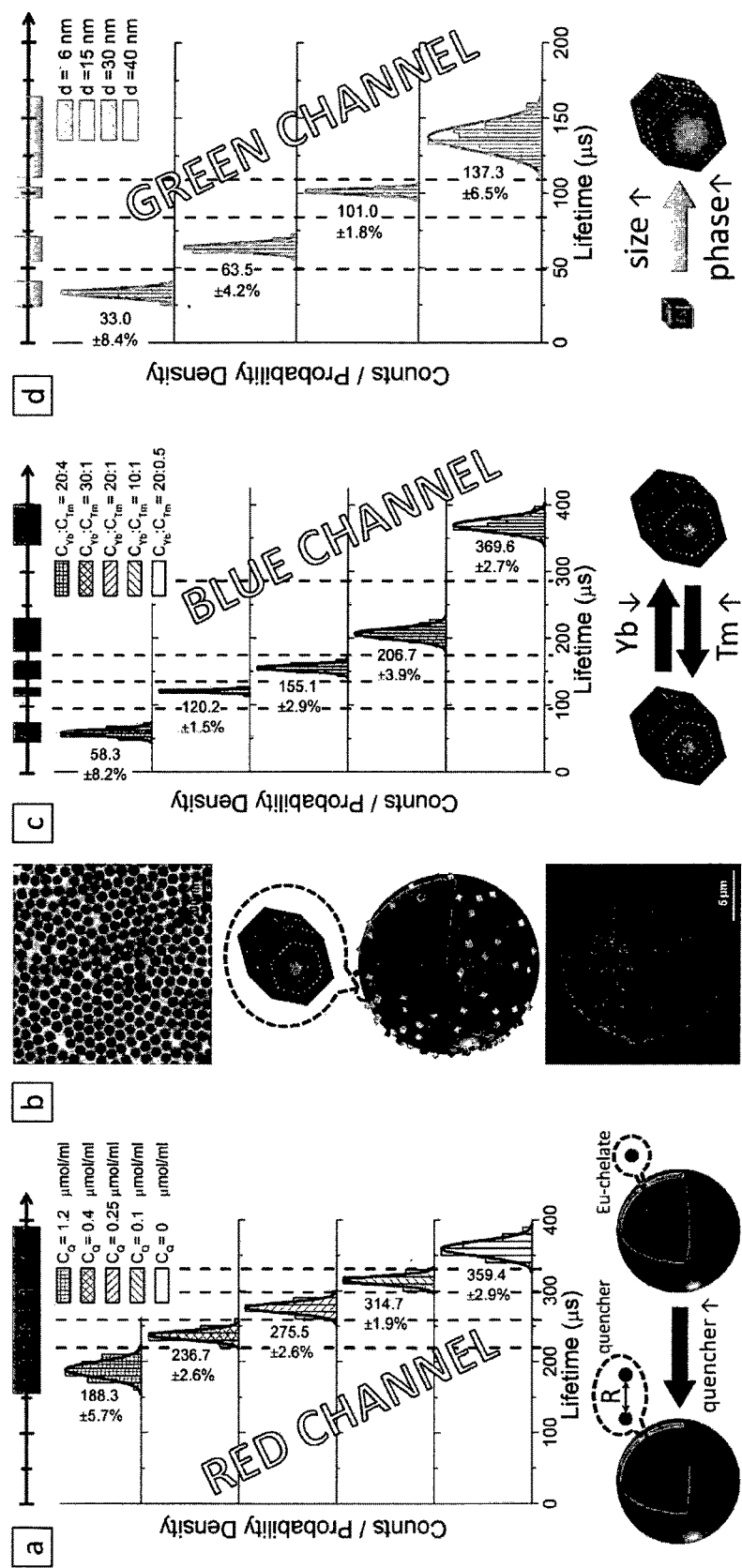
FIG. 2 illustrates example methods to encode microsecond-domain time-resolved suspension arrays by lifetime histograms of individual microspheres. In particular (a) a luminescence resonance energy transfer method, (b) an example suspension array assembly by upconversion nanocrystals as building-blocks, (c) an upconversion energy transfer method by adjusting the differential concentration of sensitizer-activators, and (d) a size-dependent luminescence method, by tuning both size and phase of upconversion nanocrystals.

Referring to FIG. 2a, there is illustrated an example luminescence resonance energy transfer method or process. By adding incremental amounts of quencher dyes, one can tune rare earth or lanthanide complex lifetimes, for example europium complex lifetimes, to generate an increased number of populations of microspheres, for example 2, 3, 4, 5 or more than 5 populations of microspheres.

In order to introduce fluorophores into microspheres, a method of solvent swelling using an organic solvent is used, allowing the dye molecules to infiltrate the microspheres.

When these microspheres are subsequently transferred into aqueous solution the microspheres shrink and both donor and acceptor dyes become uniformly entrapped. Individual single microspheres were scanned by a prototype time-resolved scanning cytometer where 615 nm (donor europium emission) luminescent lifetimes of single microspheres were plotted into a histogram as shown in FIG. 2a.

Increasing acceptor concentrations resulted in enhanced LRET efficiency, and accelerated the decay rate of europium donors, consistent with the established formula of LRET. This allows lifetime populations to be coded and decoded.

The lifetime CV was in the range of 1.9% to 5.7%. An alternative method to generate more lifetime populations is through application of a different rare earth complex, for example a different europium complex such as the new europium complex BHHBCB, 1,2-bis[4'-(1",1",1",2",2",3",3"-heptafluoro-4",6"-hexanedion-6"-yl)benzyl]-4-chlorosulfobenzene, having a much longer luminescence lifetime of 520 µs.

Upconversion Nanocrystals (UPNC) for Tuning Luminescent Decay Rates

A second technique, method or mechanism to precisely or accurately tune micro- and/or milli-second luminescent decay rates is based on rare-earth doped upconversion nanocrystals (UPNC). In this example, a probe or nanocrystal is typically co-doped with thousands of ytterbium (Yb3+) sensitizers and erbium (Er3+) or thulium (Tm3+) emitters, which significantly amplifies the overall intensity per single crystal at tunable size from a few nm to tens of nm. The internal multiphoton sequential energy transfer from the sensitizer (Yb3+) to activator (Er3+) or (Tm3+) can be used to produce individual lifetime-tunable nanocrystals as building blocks to assemble into the lifetime and emission coded probes or microspheres (also referred to as super-beads or mega-beads).

This mechanism was firstly demonstrated by co-doping the Yb to Tm at varied concentrations and ratios in $NaYF_4$ nanocrystals, which were encapsulated into microspheres by a simple swelling method.

Referring to FIG. 2b-d, there is illustrated (b) suspension arrays that can be assembled by upconversion nanocrystals as building-blocks; (c) a method of upconversion energy transfer, by adjusting the differential concentration of sensitizer-activators more than 5 populations of Tm microspheres at blue band can be generated; (d) a method of size-dependent luminescence, by tuning both size and phase of upconversion nanocrystals another 4 populations of Er microspheres at green band can be generated. The numerals to the left of each histogram of populations are the mean lifetime±the lifetime CV from Gaussian statistics fitting.

Though the multiphoton energy transfer introduced a nonlinear relationship between the sensitizer-activator distance and luminescence decay rate, interestingly, the Tm variation of 0.5%-4% (Yb fixed at 20%) resulted in a significantly large range of lifetimes from 58.3 µs to 369.6 µs at ~474 nm, while an increase of Yb concentration from 10% to 30% (Tm fixed at 1%) also significantly accelerated the blue emission decay from 206.7 µs to 115.4 µs. These results were obtained with a time-resolved upconversion scanning cytometer.

This clearly realized another five completely separated lifetime channels at the blue band. The demonstrated lifetime CV dynamic range was from as low as 5% up to 8%. The narrow CV and continuous tunable lifetime range by either Yb or Tm variation could easily support up to seven lifetime channels.

Size and Phase of Upconversion Nanocrystals (UPNC) for Tuning Luminescent Decay Rates A third technique, method or mechanism to precisely or accurately tune micro- and/or milli-second luminescent decay rates is based on the lifetime-tunable feature of different size and phase of upconversion nanocrystals, such as NaYF4:Yb, Er. When Yb and Er doping concentrations were fixed at 20% and 2% respectively, cubic phase crystals typically yield shorter lifetime than hexagonal phase crystals due to an increased level of crystal defects and internal quenching, and smaller-sized crystals emit shorter lifetime luminescence due to higher surface quenching by large surface-to-volume ratio.

In a particular example, by encapsulating 6 nm (cubic), 15 nm (cubic), 30 nm (hexagonal) and 40 nm (hexagonal) nanocrystals into microspheres, four clearly separated lifetime channels were created in a green band, with statistical lifetime histograms plotted in FIG. 2d. For example, microspheres prepared by advanced nanocrystal self-assembly techniques achieved a green luminescence lifetime of about 200 μs. Thus, it is possible to create about five or more lifetime channels in the green band, for example between about 33 μs (for 6 nm, cubic) to about 200 μs. Alternatively different nanocrystal host materials, such as $Y_2O_3$ nanocrystals, having slightly higher phonon energies, can quench the luminescence decay rate.

Figure 3:
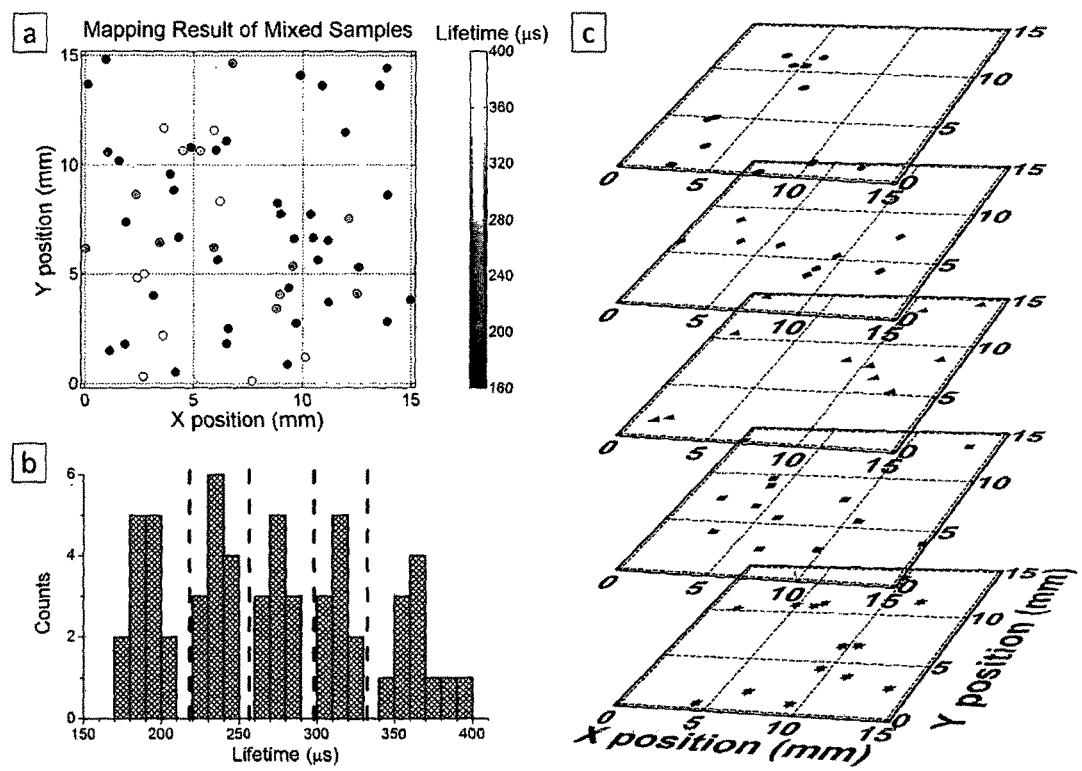
FIG. 3 illustrates an example mapping of individual microspheres, and time-resolved separation of five Red populations carrying coded lifetimes.

Referring now to FIG. 3, there is illustrated mapping of example individual microspheres, and time-resolved separation of five Red populations carrying coded lifetimes. The gray scale bar represents the lifetime values. When mixing different lifetime populations of microspheres, the decoding system can accurately separate them into their original lifetime groups. This shows no crosstalk between neighborhood lifetime populations.

To further evaluate time-resolved suspension arrays, the five families of europium LRET microspheres were mixed together and deposited onto a glass slide. An area of 15×15 $mm^2$ of the sample was analyzed using a time-resolved scanning cytometer. After 3 minutes rapid scanning, the positions of the mixed microspheres where localized on x-y coordinates as shown in FIG. 3a, and the variant lifetimes of single microspheres were then decoded as gray intensity tones. From the lifetime histogram (see FIG. 3b), the same boundaries in FIG. 2b can be clearly recovered to distribute the mixed sample into the original five sub-populations (see FIG. 3c). This approach indicates that the multiplex assay technique using suspension arrays provides a randomly distributed solid-phase analog of the planar array multiplexing method. This example shows results for a multiplexing detection process for lifetime-encoded Eu-LRET example microspheres, using time-resolved scanning cytometry. FIG. 3a shows an example mapping result (in this example locations on a microscopic slide) of a mixture of five selected types of Eu-LRET microspheres. The tones bar represents the lifetime values. FIG. 3b shows individual types of microspheres in the mixed sample are recognized based on the separation of lifetime populations using definite boundaries in between. FIG. 3c shows the initial mapping result for the mixed sample is thus decomposed into five planes of different lifetime regions for individual types of Eu-LRET microspheres carrying lifetime identities.

In one particular example, polymer microspheres were doped with four types of lanthanide probes at respective concentrations: two are down-conversion luminescence materials: Eu chelates or Eu nanocrystals emitting red luminescence (615 nm), Tb complexes or Tb nanocrystals, both of which only emit luminescence under UV (<400 nm) excitation, and two are upconversion luminescence materials: Tm UPNCs emitting blue luminescence (475 nm), and Er UPNCs emitting green luminescence (545 nm), both of which only emit luminescence by IR illumination. Moreover, their radiative decay profiles are delicately engineered, resulting in distinct lifetimes for each emission wavelength.

Referring to FIG. 1, there is illustrated an example decoding concept of time-resolved suspension arrays. They are long-lived luminescence microspheres with engineered distinct luminescent lifetimes, and randomly distributed on a microscope slide. (a) It typically takes a wide-field scanning microscope, for example as disclosed in the Applicant's co-pending International Application No. PCT/AU2103/000559 incorporated herein by reference, to map these beads (microspheres) in background-free condition by UV LED pulsed excitation and time-gated luminescence detection in anti-phase. The signal train profile (bottom) indicating the transit of the microcarriers, are used to detect the locations of individual microspheres. (b) The position coordinates guide orthogonal spot-by-spot inspection of target beads in the centre of wide-field microscopy view, so that the optical lifetime codes of single microspheres can be simultaneously decoded at blue band (470-490 nm or 520-560 nm from terbium emission) and red band (610-625 nm europium emission) under pulsed UV (365 nm LED) illumination, and blue band (450-490 nm thulium emission) and green band (525-545 nm) under pulsed IR (980 nm LD) illumination. The europium and terbium emissions under IR illumination are invisible and the erbium and thulium emissions are invisible under UV illumination. These microspheres are completely invisible under visible light excitation.

Figure 4:
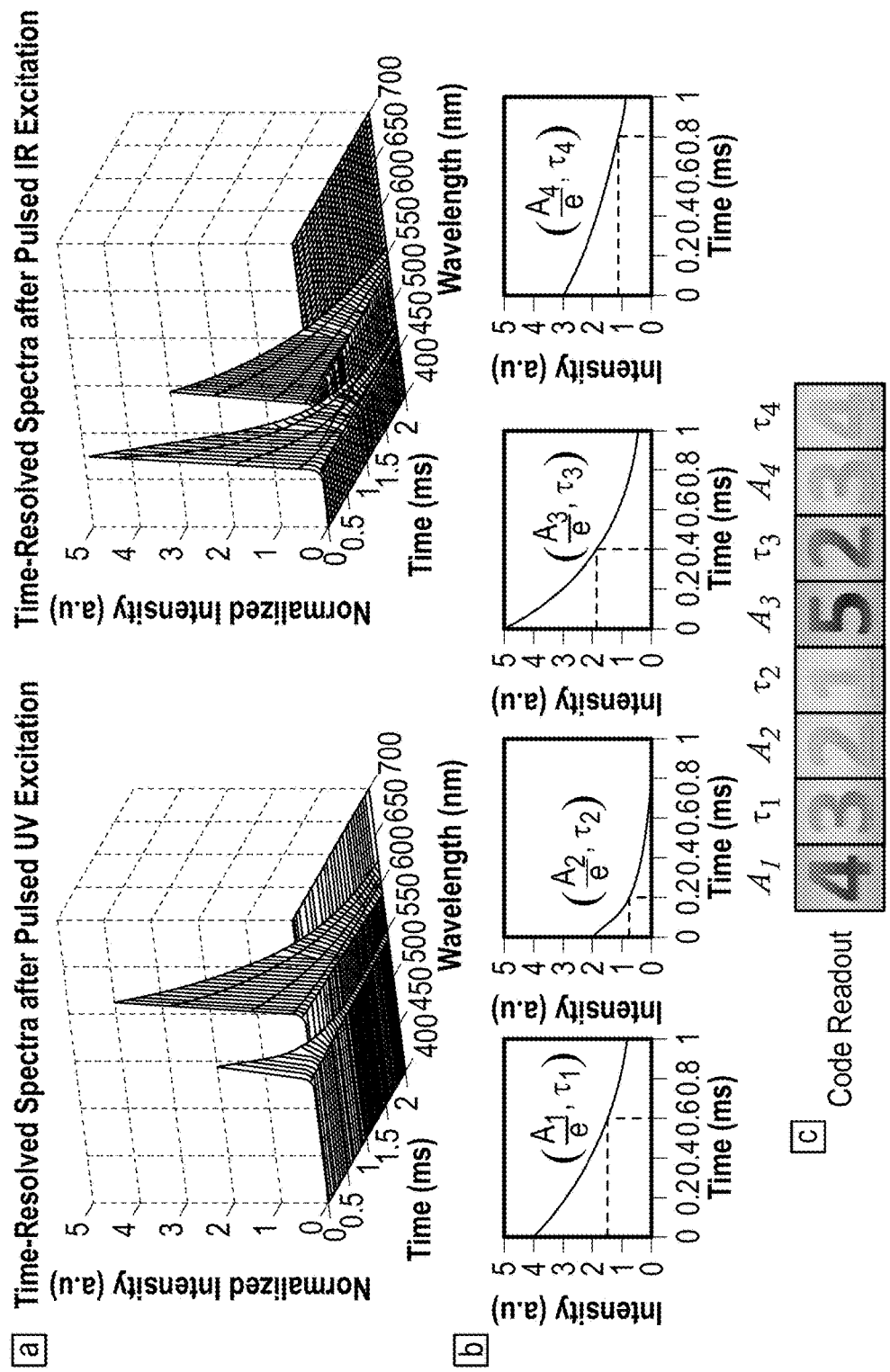
FIG. 4 illustrates a three-dimensional time-resolved spectrum for example encoded microspheres after application of UV and IR pulsed excitation beams (a), which can be decomposed into four channels using band-pass colour filters, each channel has its own initial intensity and decay lifetime as two independent parameters (b), leading to a total of eight dimensions as eight digits (c).

FIG. 4 illustrates that after application of a UV pulsed excitation beam and a IR pulsed excitation beam, each encoded microsphere presents a three-dimensional time-resolved spectrum (see FIG. 4a), which can be decomposed into four channels using band-pass colour filters. Each channel has own initial intensity and decay lifetime as two independent parameters (see FIG. 4b), leading to a total of eight dimensions as eight digits (see FIG. 4c). By controlling the conditions of chemical syntheses, these intensities and lifetimes are capable of being engineered to discrete levels, thereby allowing unique codes to be digitized (see FIG. 4c). For example, if five distinct levels can be generated for every digit, this time-resolved encoding strategy provides $5^8$ combinations, significantly surpassing the prevailing known suspension array method based on colour vs. intensity. As another example, if four distinct levels can be generated for every digit, this time-resolved encoding strategy provides $4^8$ combinations.

Using various examples, the Applicant successfully obtained 5 (Eu: red)×5 (Tm: blue)×4 (Er: green)=100 non-crosstalk lifetime channels. There are at least two more spectral bands of lifetimes under UV excitation (Tb 545 nm; Pt 700 nm), which are spectrally separated from the existing lifetime channels. This extends the practical lifetime codes for suspension arrays to a level of about $5^5=3125$. The terbium (Tb) luminescence can be generated from either terbium complex, such as $Tb(PTA)_3phen$, or a terbium down-conversion nanocrystals, such as GdOHCO3:Tb.

Creating lifetime multiplexing channels, such as using rare-earth luminescence based microspheres, provides, for example, the following advantages.

1. Lifetime is less prone to decoding errors induced by ambient background and electronic noise, since it is based on a decay profile rather than absolute intensity measurements.

2. The time-resolved detection of exceptionally long luminescence in the microsecond domain can significantly or completely suppress all the autofluorescence background from usually complex biosamples, as well as a surface bound reporter dye on beads.

3. Rare-earth materials employed only emit luminescence under UV (300 nm to 370 nm) and infrared (976 nm) irradiation, thus these optical codes remain dark when exciting the microspheres' or beads' surface by visible light for bioassays.

4. The decoding instrument is relatively simple, including two diode sources (for example 365 nm and 976 nm diodes) and single detector design.

Further Examples

The following examples provide a more detailed discussion of particular example embodiments. The examples are intended to be merely illustrative and not limiting to the scope of the present invention.

Preparation of Microspheres Encoded with Upconversion Nanocrystals and LRET Dyes Microsphere beads (~15.14 µm, 2.6×10$^5$) were swelled in a 200 µl solvent mixture containing 5% chloroform and 95% butanol (vol/vol) for 1 h. Then the upconversion nanocrystals (25 µl, 20 mg/ml) and 2.5 µmol Eu(TTFA)$_3$ with designated molar quantity of quenching dye in 25 µl cyclohexane were thoroughly mixed, followed by the incubation with as-prepared swollen beads. This incubation process was allowed for 24 h, which encapsulates fluorescent nanocrystals and dyes into polystyrene microspheres in a single step. Finally, the encoded beads were isolated by centrifugation, washed by ethanol:water (vol/vol=1:1) and absolute ethanol for several times, and redispersed in DI water.

Upconversion Nanocrystals (UPNC) Synthesis

NaYF$_4$:Yb,Tm and NaYF$_4$:Yb,Er were synthesized using organometallic methods. Briefly, 5 ml of methanol solution of LnCl$_3$ (1.0 mmol, Ln=Y, Yb, Tm/Er) together with 6 ml OA and 15 ml ODE were added to a three-neck round-bottom flask. The resulting mixture was heated at 150° C. under argon flow for 30 min to form a transparent, yellow solution. After cooling down to 50° C., 10 mL of methanol solution containing 0.16 g NH$_4$F and 0.10 g NaOH was added with vigorous stirring for 30 min. Then, the slurry was slowly heated to 110° C. for 30 min under vacuum to remove methanol and a small amount of water. Next, the reaction mixture was protected with argon atmosphere, quickly heated to 305° C. and maintained for 1.5 h. A large amount white smoke was generated during this process. The solution was cooled down and the products were isolated by adding ethanol and centrifugation without size-selective fractionation. The resulting NaYF$_4$:Yb,Tm/Er nanocrystals were redispersed in cyclohexane with 10 mg/ml concentration.

Preparation of Microspheres Encoded with UPNCs

The incorporation of nanocrystals into microspheres for encoding can be achieved by any of the following steps.

(i) The nanoparticles can be captured or affinity partitioned in the surface or subsurface of as-prepared microspheres.

(ii) The nanoparticles can be bound onto the oppositely charged microspheres via a layer-by-layer strategy.

(iii) The nanoparticles can be loaded during the polystyrene microspheres synthesis, either by emulsion or suspension polymerization.

The upconversion nanocrystals were prepared using the method described above. Briefly, the swelling beads (2.6× 10$^5$ beads) were obtained in a 200 µL solvent mixture containing 5% chloroform and 95% butanol (vol/vol) with mild stirring for 1 h. The nanocrystals (50 µl, 10 mg/ml) were mixed and incubated with a polystyrene beads dispersion. The incorporation process lasted for about 12 h at room temperature through hydrophobic-hydrophobic interaction. Finally, the tagged beads were collected by centrifugation, washed three times with ethanol, and redispersed in deionized water.

Figure 5A:
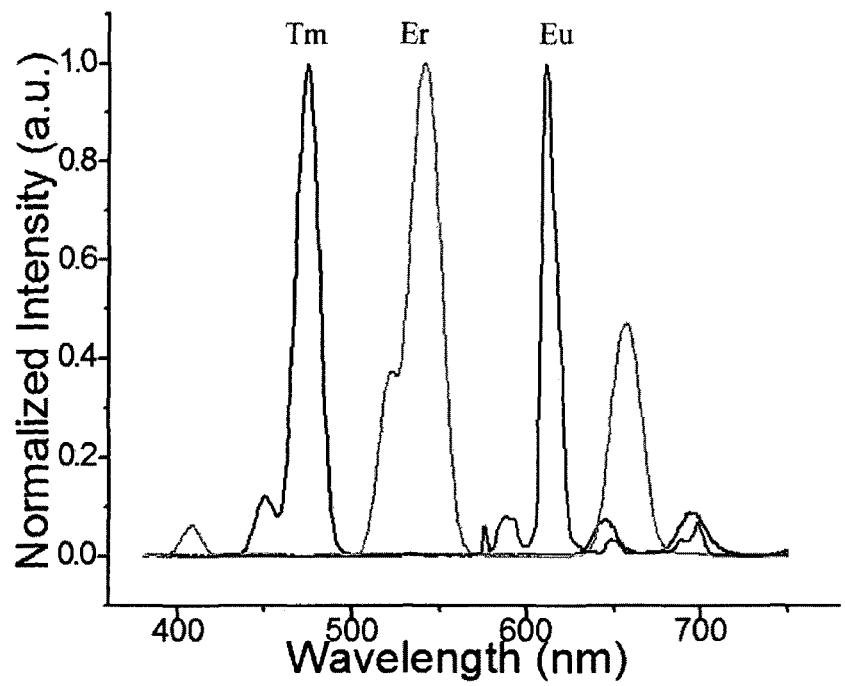
FIG. 5a shows normalized emission spectrum of Eu chelates (under 365 nm), Er and Tm upconversion nanocrystals (under 980 nm).

Lifetime Measurement of Microspheres and Crosstalk Among Different Colour Channels FIG. 5a illustrates the spectra of Eu(TTFA)$_3$ chelates, NaYF$_4$:Yb,Er upconversion nanocrystals and NaYF$_4$:Yb, Tm upconversion nanocrystals. The Eu chelates are excited by 365 nm UV-LED, which cannot excite Er/Tm nanocrystals to light up. Likewise, upconversion process under 980 nm IR-laser only occurs in Er/Tm nanocrystals. Sequential operation of excitation wavelength was applied, ensuring no interference between Eu channels and upconversion channels.

Both Tm-doped blue-emitting nanocrystals and Er-doped green-emitting nanocrystals absorb 980 nm photons. Therefore, considerations need to be given in order to avoid serious spectral overlapping, which generally happens with other fluorescent probes. In order to separate the blue upconverted luminescence from Tm nanocrystals from the green upconverted luminescence from Er nanocrystals, individual band-pass colour filters were inserted to select spectral-confined emission.

Figure 5B:
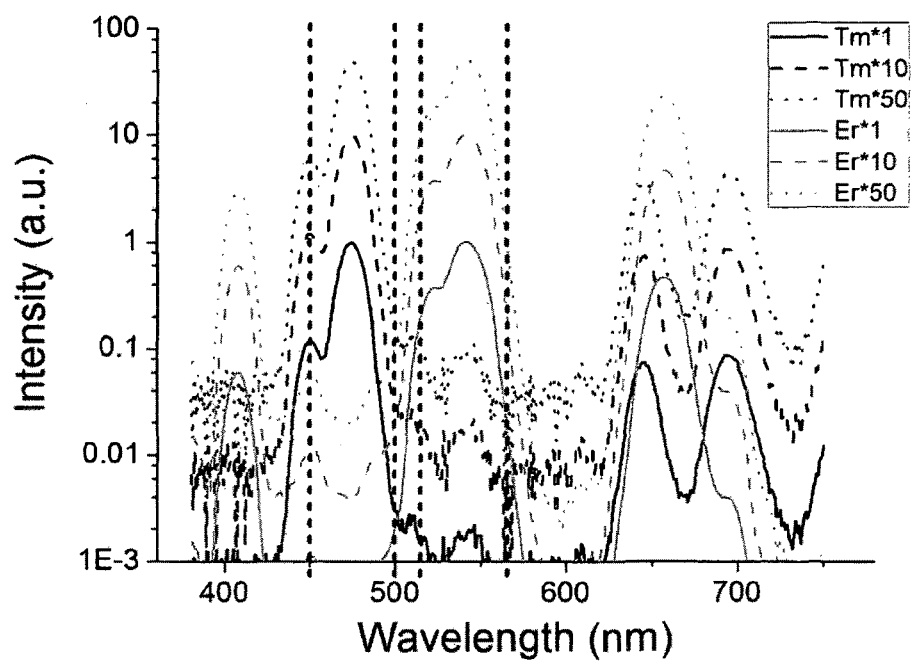
FIG. 5b shows spectral overlapping between Er and Tm emission bands when their intensities are at different levels.

As seen in FIG. 5b, the leakage from one type of nanocrystals to the detection band of the other type of nanocrystals is only about 0.1% when they have similar intensities. Leakage remains around 1% even if one intensity is 10 times brighter than the other, although the tail of emission spectrum apparently contributes to the detection band of the other. To ensure no crosstalk in lifetime channels, differences in intensity levels more than 10 times are, optionally, not allowed, since this kind of interference could not be removed in subsequent lifetime calculations. This was achieved via controlling the amount of nanocrystals added to the initial micro-emulsion suspension. For example, if it is found in one lot of microspheres that the blue emission is more than 10 times stronger than the green emission, then this lot was discarded and a new lot with less Tm nanocrystals or more Er nanocrystals was used.

Experimental verification was carried out to investigate crosstalk (i.e. whether lifetime affected) due to spectral overlapping. The Er nanocrystals and Tm nanocrystals used were intentionally selected to have substantially distinct lifetimes, so that small amounts of crosstalk could be identified. Eu complexes were also incorporated to test the non-crosstalk assumption under sequential excitation between UV and IR, with a moderate lifetime population used. Three types of probes were embedded.

Figure 5C:
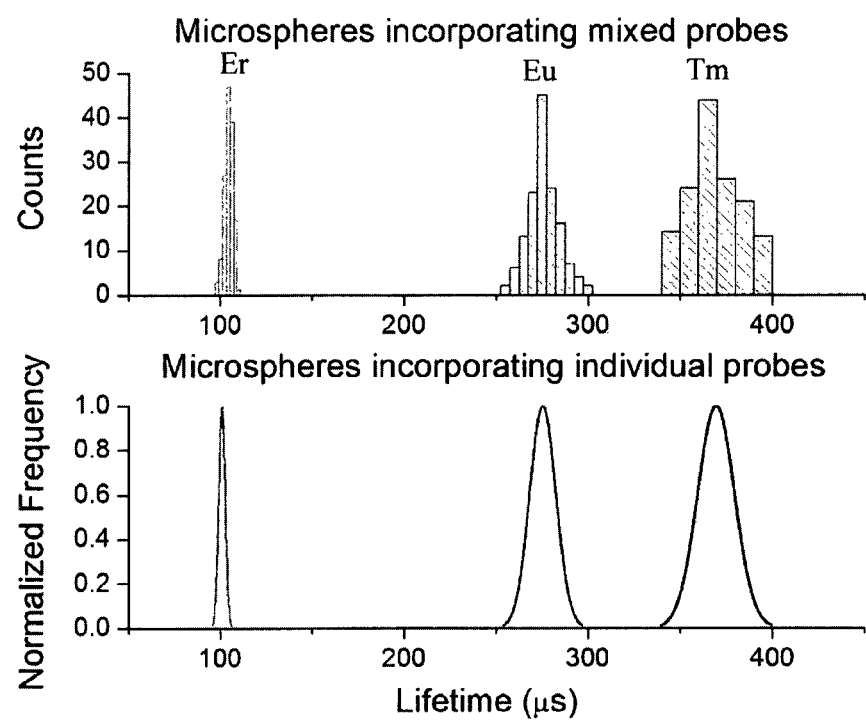
FIG. 5c shows lifetime measured for example microspheres incorporating mixed probes (Eu, Er and Tm), in comparison to microspheres incorporating the same individual probes.

A group of microspheres was incorporated using Eu complexes with 0.25 µmol/ml quencher in the LRET solution, Tm nanocrystals of 20:0.5 Yb:Tm co-dopant concentration, and Er nanocrystals of ~30 nm in diameter. A slide sample was scanned, and 142 microspheres found and measured for lifetimes of red, blue and green channels. The histogram result is shown in the upper panel of FIG. 5c. In comparison, the lifetime distributions of microspheres incorporating single type of probes were plotted in the lower panel of FIG. 5c, suggesting that the mixture of the probes did not induce any crosstalk for lifetime measurement.

Time-Resolved Scanning Cytometry

In order to detect and recognize the six-digit multiplexing probes or microspheres, a prototype time-resolved scanning cytometer was developed based on an Olympus IX71 inverted microscope frame. The cytometer includes two subsystems operating together: the scanning subsystem and the detection subsystem. In the scanning subsystem, a motorized stage (for example model H101A, from Prior Scientific) moves a solid substrate containing the sample to be tested, such as a microscopic glass slide, in a serpentine scanning pattern. As the movements are predetermined and well calibrated, the motorized stage provides precise positions of the sample at every time point during scanning. The detection subsystem has physical similarity to a common epi-fluorescence structure, but differs in the temporal sequences of operation. Rather than being switched on and off simultaneously, the excitation source and the detector (for example model H10304-20, from Hamamatsu) are electronically modulated in antiphase, referred to as the Time-Gated Luminescence (TGL) mode. The detection subsystem is capable of discovering targets emitting long-lived luminescence only, rendering any prompt decays of auto-fluorescence and scattering invisible to the detector. Considering the lanthanide probes applied in this example embodiment, a 365 nm UV LED (for example model NCCU033A, from Nichia, 250 mW at 500 mA continuous injection current) and a 980 nm IR laser were selected as the excitation sources, coupled to respective dichroic filters (for example FF511-Di01 for UV LED, transmission band 525~800 nm; FF750-SDi02 for IR laser, transmission band 450~730 nm; from Semrock) in the dichroic wheel of the microscope. Three band-pass filters were placed in a filter wheel before the detector to match different emission peaks (FF01-607/36 for Eu chelates, centre wavelength 607 nm, full width at half maximum (FWHM) 42.5 nm; FF02-475/50 for Tm UPNCs, centre wavelength 475 nm, FWHM 55.7 nm; FF01-540/50 for Er UPNCs, centre wavelength 540 nm, FWHM 55.6 nm; from Semrock). The two subsystems were synchronized via a multi-function data-acquisition card (for example model PXIe-6358, from National Instruments) and controlled by a custom Labview program.

On a microscopic slide sample, all spots containing the microspheres were localized with great accuracy, since their time-resolved luminescence is in sharp contrast against the background. The individual spots were then retrieved by turns to measure the decay profiles for the purpose of calculating the intensities and lifetimes. Consequently, the code of each microsphere reveals the type of the assay, for example type of bioassay, it is conducting, and the result can be identified as is conventionally done, for example in immunofluorescent assays.

Preparation of Eu-LRET Microspheres and Slide Samples

A series of solutions was prepared from the fixed 2.5 µmol Eu(TTFA)$_3$ complex with varied molar quantities of hexafluorophosphate salt ranging from 0.1~1.2 µmol in separate volumes of 200 µl dichloromethane (DCM). Encapsulation of fluorescent dyes into microspheres was performed by drop-wise addition of the controlled amount of donor and acceptor mixture in polystyrene bead suspension (15.14 µm in diameter, Bangs Laboratories, US; $2.6 \times 10^5$ beads in 900 µl ethanol, ultrasonically treated prior to use). The dye-containing polystyrene beads were allowed to stir for 48 hours, and then the swollen beads were shrunk in absolute ethanol solvent. Then, the impregnated beads were quickly isolated by centrifugation and then washed in ethanol:water (vol/vol 1:1) three times, and stored in 500 µl deionized water. To prepare a test sample, certain amount of microsphere dispersions typically containing 300~500 beads were drop-cast onto the surface of a glass slide. Following 4 hours incubation at 40° C. to allow complete evaporation of the solvent, the samples were sealed by glass cover slips for scanning cytometry analysis.

Multiplexed DNA Detection Application

Target DNA sequences of four kinds of pathogens—human immunodeficiency virus (HIV), Ebola virus (EV), hepatitis B virus (HBV), and human papillomavirus 16 (HPV-16)—were identified from the NCBI database. Amino-modified capture DNA oligos and 5'-biotin-conjugated target DNA oligos were purchased from Integrated DNA Technologies. Each 50 µL of as-prepared Eu-LRET lifetime-encoded microspheres were used to conjugate each type of capture probes, respectively, activated by 1-Ethyl-3-[3-dimethylaminopropyl]carbodiimide hydrochloride (EDC, purchased from Sigma Aldrich) for 2 hours. The functionalized microspheres were harvested by centrifugation and then mixed to form a test panel. Then, a test sample containing 5 nmol of each pathogen DNA oligos was added into the test panel, and 2× saline-sodium citrate (SSC, purchased from Invitrogen) buffer was used as the hybridization buffer. After 1 hour of incubation, the microspheres were washed and resuspended into 100 µl solution containing 50 µg/ml streptavidin-conjugated Pacific Orange (Invitrogen), and then incubated for another 1 hour. Finally, the suspension of microspheres were purified and prepared onto a glass slide for analysis by the time-resolved scanning cytometry.

Example lifetime-tunable luminescent microspheres for calibrating the time-resolved scanning cytometry system were produced through the luminescence resonance energy transfer (LRET) mechanism. A trivalent europium complex Eu(TTFA)$_3$ and a coumarin hexafluorophosphate were encapsulated into porous polystyrene beads as donor and acceptor dyes, based on a simple method of solvent swelling. As a result of dipole coupling when in close proximity, a proportion of excited Eu$^{3+}$ complexes transfer their energy to acceptor dyes in non-radiation manner. This leads to shortening of the luminescence lifetime of Eu$^{3+}$ complex at red emission band around 612 nm. By varying their concentrations stepwise, one can thus manipulate the average donor-to-acceptor distance, making it possible to fine-tune the lifetimes of the microspheres in corresponding steps as well.

Figure 6:
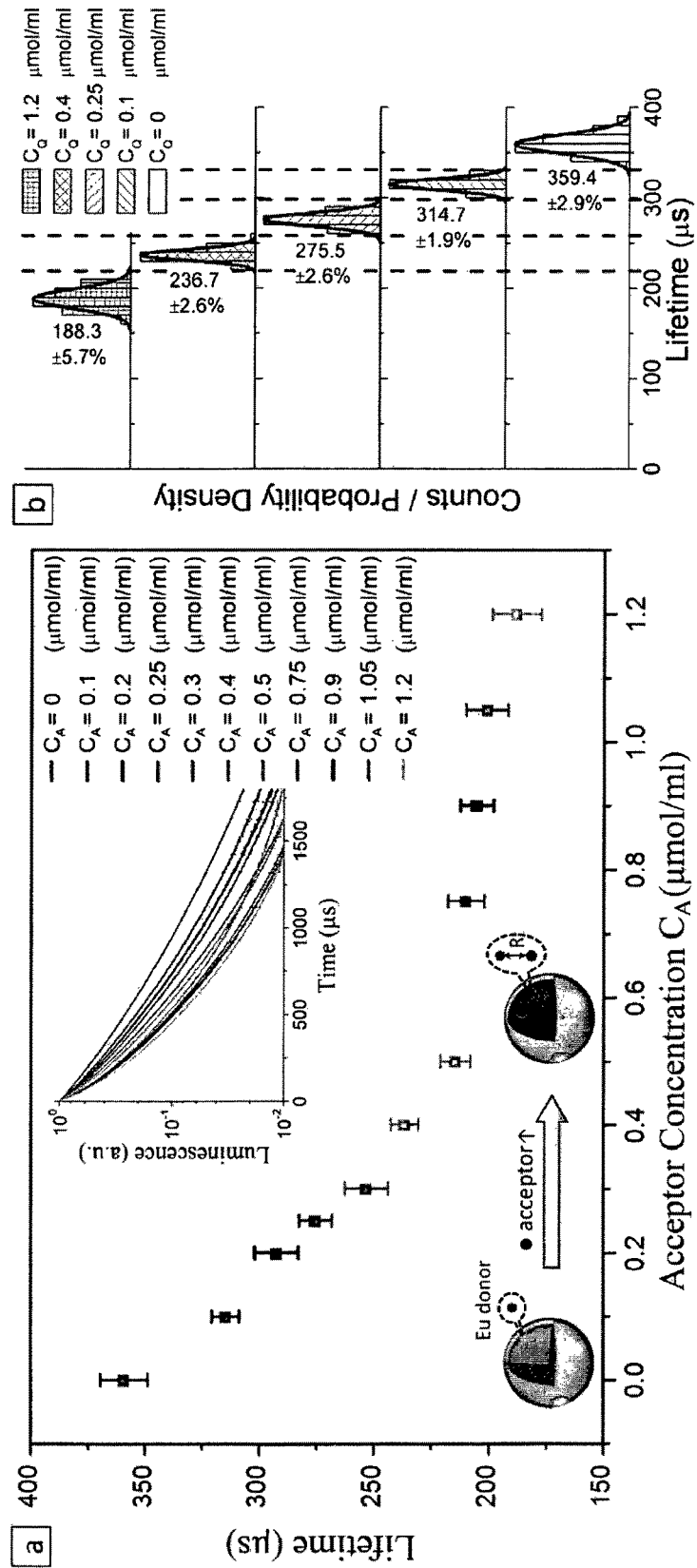
FIG. 6 illustrates example lifetime measurement results from individual Eu-containing microspheres engineered by LRET. Different solutions containing identical amounts of Eu complexes as donor but incremental amount of acceptor dyes were encapsulated into individual groups of polymer microspheres, followed by time-resolved scanning cytometry analysis. (a) Shows the luminescence lifetime measured at $Eu^{3+}$ red emission band shortens as the acceptor concentration in the original dye solution increases, as a result of stronger LRET effect. The inset curves are the luminescence decay signals measured from single Eu-LRET microspheres. (b) Shows that among the example samples, five types of example microspheres give completely separate lifetime histograms (as in FIG. 2a), so that they are capable of definite discrimination by time-resolved scanning cytometry. The numerals at the left of each histogram are the mean lifetime±the lifetime CV for its Gaussian fitting.

FIG. 6a illustrates that as the acceptor concentration increases (at identical donor concentration), the donor lifetime is effectively tuned down from 359 µs to 188 µs, measured from individual microspheres by a time-resolved scanning cytometry system/method. Each lifetime population has a coefficient of variation (CV) in the range of 1.9% to 5.7%, allowing the well-controlled lifetime properties to serve as time-domain optical identities. Among the as-prepared Eu-LRET microspheres, five populations (acceptor concentrations at 0, 0.1, 0.25, 0.4 and 1.2 µmol/ml) can be completely separated solely based on lifetime (mean±CV: 359.4 µs±2.9%, 314.7 µs±1.9%, 275.5 µs±2.6%, 236.7 µs±2.6% and 188.3 µs±5.7%), which is shown in FIG. 6b.

It should be noted that the LRET mechanism employed to produce the Eu-LRET microspheres did not necessarily keep the luminescence decays as monoexponential, which can be seen from the recorded decay curves in FIG. 6a. However, the purpose of engineering as well as measuring lifetimes is to use a lifetime parameter as a distinguishable identity for multiplexed biodetection. Important requirements are reliability and speed in order to guarantee the accuracy and throughput for lifetime decoding. Hence, the curves were fitted with a monoexponential model in this example, and the calculated lifetimes are in truth apparent lifetimes reflecting the weighted averages of all lifetime components.

Figure 7:
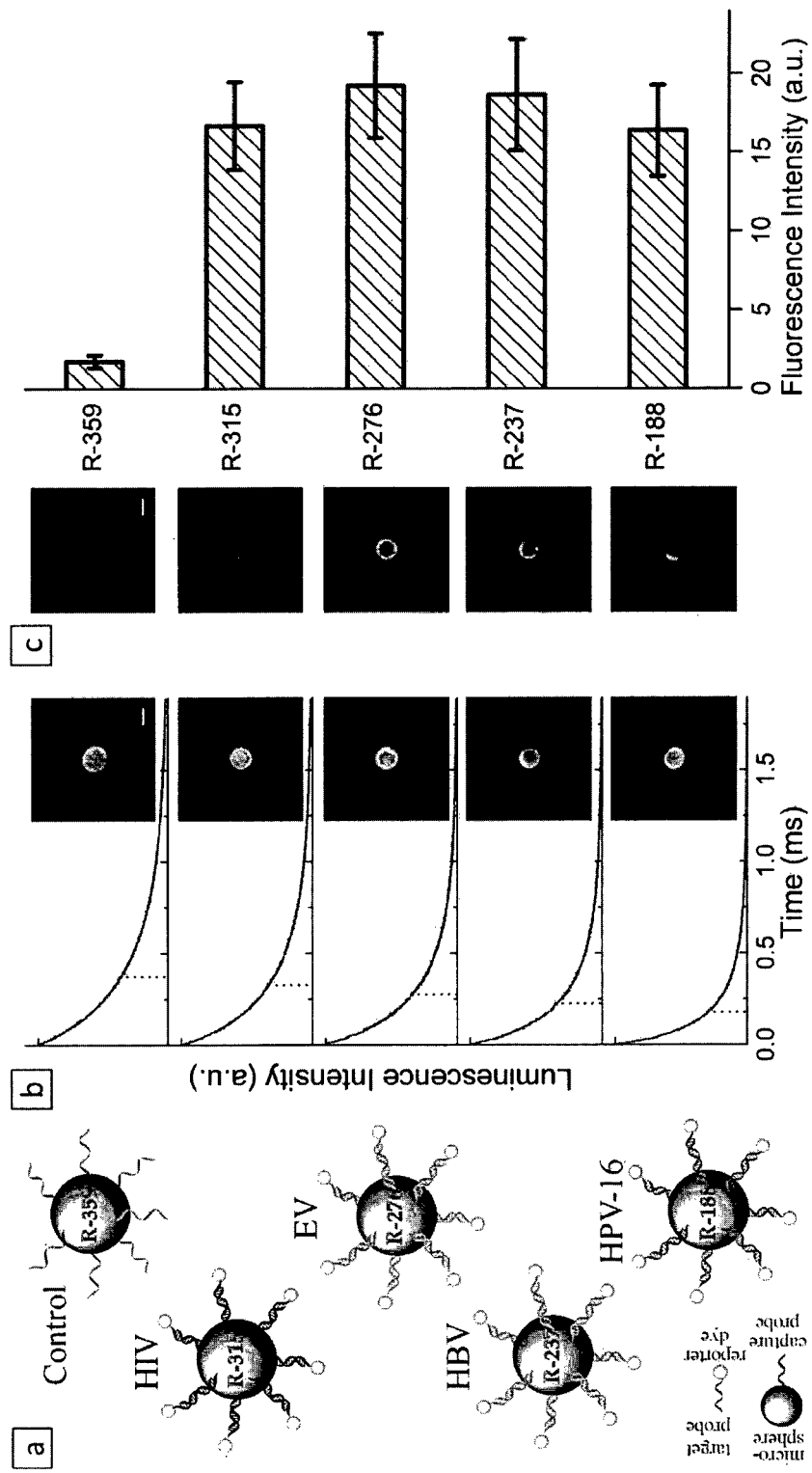
FIG. 7 illustrates an example demonstration of multiplexed DNA detection using lifetime-encoded Eu-LRET example microspheres and time-resolved scanning cytometry. (a) The five selected types of Eu-LRET microspheres (refer to FIG. 6b) were conjugated to five different capture probes of DNA sequences (four are complementary to pathogen DNAs from HIV, EV, HBV and HPV-16, and the other is for control purpose). A universal reporter dye was also used in the sandwich beads assay. (b) The example microspheres were identified into different types by measuring their lifetimes from $Eu^{3+}$ luminescence decays. (c) The amounts of target pathogen DNAs in the test sample were determined through measuring the fluorescence intensity of the reporter dye. Images were taken with different emission bandpass filters at 500 ms exposure time under continuous excitation. (Scale bar: 10 μm).

The five selected types of example microspheres were mixed together to further evaluate the accuracy of lifetime multiplexing detection. The mixed sample was spiked on a slide area of 15×15 mm$^2$, which was analyzed by the time-resolved scanning cytometry. After three minutes of scanning, the X-Y positions of these microspheres were located and the varying lifetimes of single microspheres were then decoded. Consequently, the time-resolved scanning cytometry distinguished every type of microsphere (therefore were categorized as R-359, R-315, R-276, R-237 and R-188; "R" stands for red colour and the numbers refer to lifetime values), which can be used to probe different biomolecules (see FIG. 7).

As an example demonstration of a biological application, the lifetime multiplexing technique was further applied to detect different pathogen DNAs (HIV, EV, HBV, and HPV-16) simultaneously. Four types of example microspheres (R-315, R-276, R-237 and R-188) were conjugated respectively to the complimentary DNA strands, which act as capture probes to each target probes. The other type of microsphere (R-359) was conjugated to a control DNA probe in order to verify the specificity of the multiplexed detection. The target pathogen DNAs were mixed as a test sample, which was added into a test panel consisting of the five types of microspheres, followed by adding pacific orange as the universal reporter dye (see FIG. 7a).

The resulting suspension was spread onto a glass slide and was analyzed using the time-resolved multiplexing system/method, which discovered all microspheres on the slide by detecting the time-gated luminescence from the $Eu^{3+}$ complex and identified their capture probes by decoding the lifetimes (see FIG. 7b), as well as measuring the amounts of corresponding target probes by checking the reporter fluorescence (see FIG. 7c). The result shows that the lifetime-coded microspheres can successfully recognize multiple pathogen DNAs in a single test, by using the standard format of sandwich beads assay. In particular, it is important to note that although the reporter dye is excited by the same light source for the $Eu^{3+}$ complex, its fluorescence does not interfere with the encoding luminescence lifetime due to their absolute discrimination in the temporal domain, while traditional multiplexing techniques based on colour and intensity typically encounter serious crosstalk issues.

The time-resolved scanning cytometry system has the capability of resolving luminescence lifetime as an independent optical identity for individual targets, for example, multiple DNA strands probed by different microspheres with their lifetimes engineered through luminescence resonance energy transfer. These results offer new opportunities to employ high-sensitivity luminescence probes, such as lanthanide complexes and nanocrystals, for lifetime-based biosensing and bioimaging, and other applications for example in security or security inks, including high-throughput multiplexed screening through time-resolved cytometry, as well as localized dynamic analyses by Fluorescence-Lifetime Imaging Microscopy (FLIM).

Tunable "τ-Dots" Providing Microsecond Time-Domain Codes—Further Applications

Optical multiplexing broadly impacts diverse fields from optical data storage and document security to molecular probes and bead assays to personalized medicine. As previously discussed, conventional fluorescent colour coding is limited by spectral overlap and background interference, restricting the number of distinguishable identities. The Applicant has realised that a new dimension of luminescent lifetimes (τ) can be exploited to code individual upconversion nanocrystals. In a single colour band, one can generate more than 10 nanocrystal populations having distinct lifetimes from 25.6 μs to 662.4 μs, and decode their non-crosstalk lifetime identities, which are substantially or completely independent from either colours or intensities. Such "τ-Dots" (i.e. luminescent lifetime probes) are readily applied to, for example, multi-channel bioimaging, high-density data storage, and security applications combating against counterfeiting.

In an example, the multiplexing method/system manipulates the luminescence decay lifetimes of upconversion nanocrystals, which allow creation of a whole new temporal dimension available for multiplexing. Lifetime multiplexing assay methods have significant advantages, for example: i) lifetimes are less prone to decoding errors induced by optical defocusing, ambient background, and electronic noise, since their readout is based on the decay profile rather than on absolute intensity measurements; ii) time-resolved detection of exceptionally long luminescence in the microsecond domain can significantly or completely suppress all autofluorescence background from usually complex biological samples or embedding substrate; iii) rare-earth doped upconversion materials employed only require diode excitation, so that decoding instrumentation can be very simple, here consisting of one laser diode and a single photo-detector.

Figure 8:
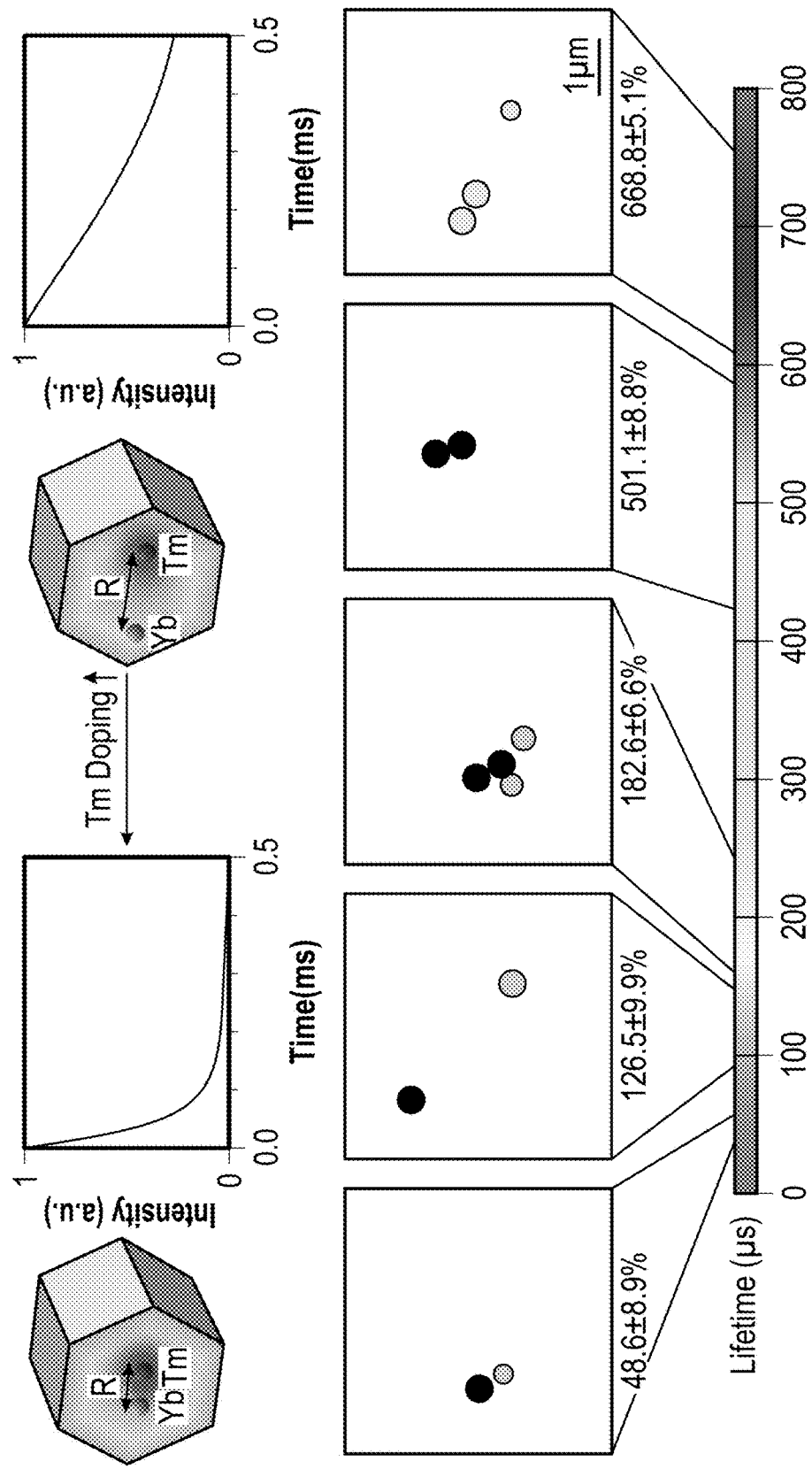
FIG. 8 shows a lifetime tuning example method and time-resolved confocal images for $NaYF_4$:Yb,Tm upconversion nanocrystals. Each pixel was excited for 200 μs followed by a delayed detection window up to 3.8 ms to record its time-gated luminescence decay. The shade or greyscale for each pixel represents its lifetime value decoded from the decay curve. The nanocrystals in the images from left to right have Tm doping concentrations of 4, 2, 1, 0.5 and 0.2 mol %, respectively.

Example multiplexing assay methods, systems, arrays and target particles based on the tunability of lifetimes have been implemented by co-doping sensitizer $Yb^{3+}$ ions and blue-emitting $Tm^{3+}$ ions at stepwise varied concentrations into the $NaYF_4$ nanocrystals. In this case, the energy transfer from the sensitizer to the emitter ion at a varying sensitizer-emitter distance provides lifetime tunability (see FIG. 8). By using this approach one can tune the lifetime from 48 μs (4 mol % Tm) to 668 μs (0.2 mol % Tm). Taking advantage of nanocrystal photostability and background-free scanning in time-resolved detection, a time-resolved confocal scanning system achieved sufficiently high signal-to-background ratio (over $10^2$) for lifetime measurement of single nanocrystal's emission at 475 nm. FIG. 8 shows the confocal images of five typical groups of lifetime-encoded thulium-doped τ-Dots, using pseudocolour/scale to map the luminescence lifetime for each pixel.

The τ-Dots emit luminescence in the microsecond range, about three orders of magnitude longer than the background autofluorescence (less than 10 nanoseconds), which can be easily suppressed through time-resolved measurements. This can be used to provide background-free readout for rapid detection of single cells.

The τ-Dots with lifetime codes can be surface functionalized, enabling bioconjugation to a number of different antibodies for simultaneously probing multiple rare-event pathogens (e.g. *Giardia lamlia, Escherichia coli* O157:H7, *Cryptosporidium parvum*) in beverages, food, or within a hospital environment, in an effort to prevent disease or infection.

Figure 9:
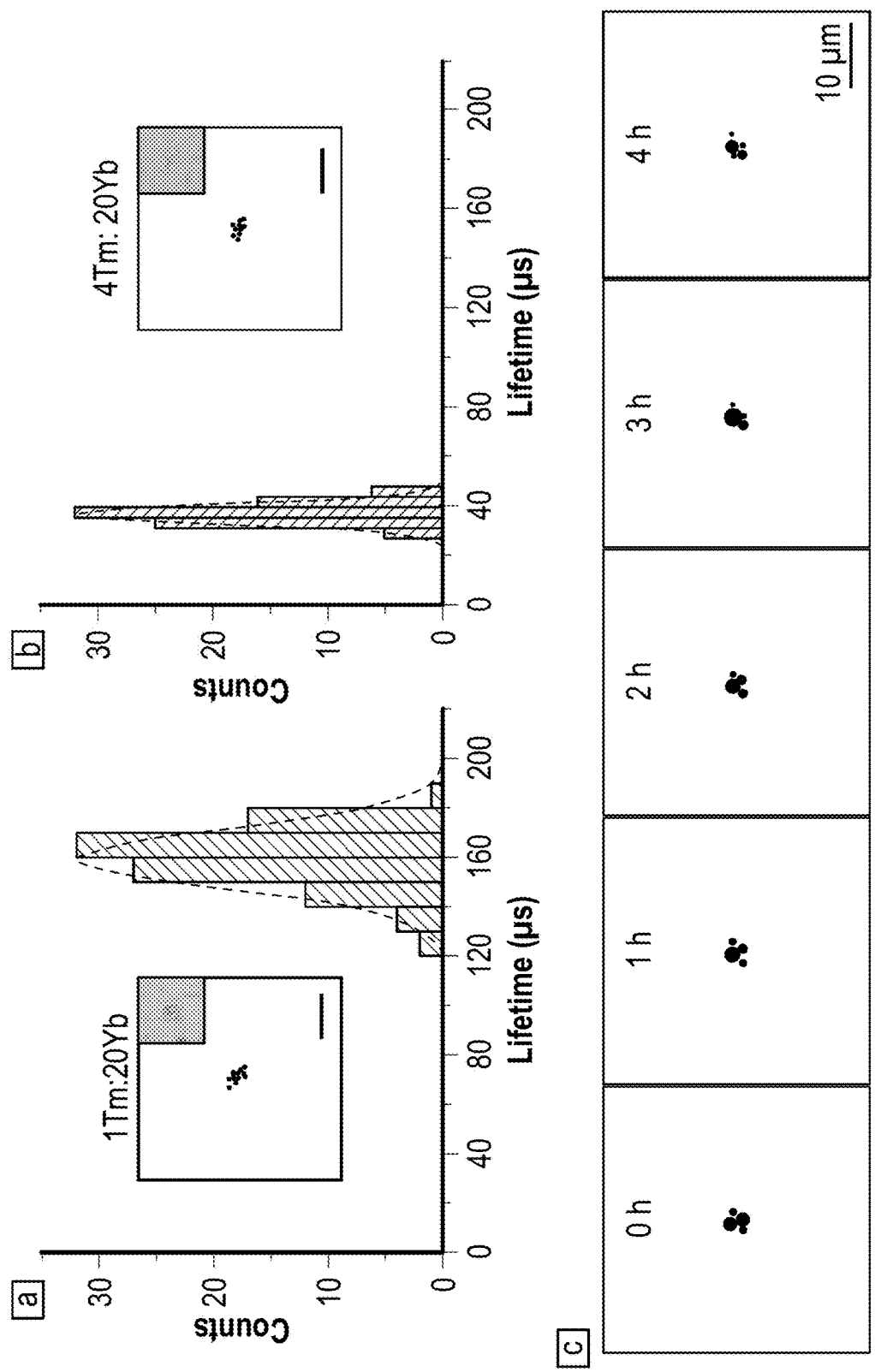
FIG. 9 shows results for example τ-Dots labelled Giardia cysts measured by a time-resolved scanning cytometry system: (a) and (b) show lifetime histograms concluded from cysts labeled with different lifetime-encoded τ-Dots (Tm/Yb codoping concentration (mol %:mol %) of 1:20 for (a) and 4:20 for (b)). The scanning cytometry allows retrieval of each individual target cysts for luminescence as well as bright-field imaging confirmation. (c) shows the typical recorded luminescence images for the same cyst under 4-hour continuous laser excitation.

FIG. 9 illustrates a simple demonstration of two populations of *Giardia lamblia* cysts labelled with the 1 mol % Tm τ-Dots at lifetime about 160 μs and 4 mol % Tm τ-Dots at lifetime about 40 μs, respectively, and rapidly scanned by the time-resolved scanning cytometry system. The lifetime parameters yield narrow population distributions (coefficient of variations<10%), offering superior detection accuracy and system simplicity in contrast to the conventional high-throughput cytometry systems which otherwise are currently suffering from both crowded colours and fluctuating intensities. This result shows the feasibility of "digital cytometry" based on the lifetime codes without colour/intensity compensation requirements. The recorded τ-Dots-stained *Giardia* images over hours of continuous illuminations show no observable photobleaching effects (FIG. 9c), indicating these lifetime-encoded nanocrystals as robust labelling materials for bioimaging.

The nanocrystals were coated with a thin silica layer. Then the modified nanocrystals (1 mg/ml) were functionalized with a universal antibody linker in a buffer solution. This unique linker has one end capable of interacting with silica to anchor on the silica surface, and the other end coupling with any antibody molecule. The anti-*Giardia* antibodies (G203, 0.44 mg/ml, cyst-wall specific, BTF Pty Ltd., Sydney, Australia) were used to incubate with above functionalized nanocrystals for 20 min, followed by low speed centrifugation to remove aggregates. The resulting nanocrystals with antibody were dispersed in 200 μl buffer solution, then mixed with 5 μl of *Giardia lamblia* preparation ($10^5$ cells in 1.8 ml, 6-9 μm in diameter, BTF Pty Ltd.) for 20 min under shaking. Finally, after washing three times with buffer, the labelled cells were spiked on a glass slide and sealed with a cover slip for scanning cytometry analysis.

Figure 10:
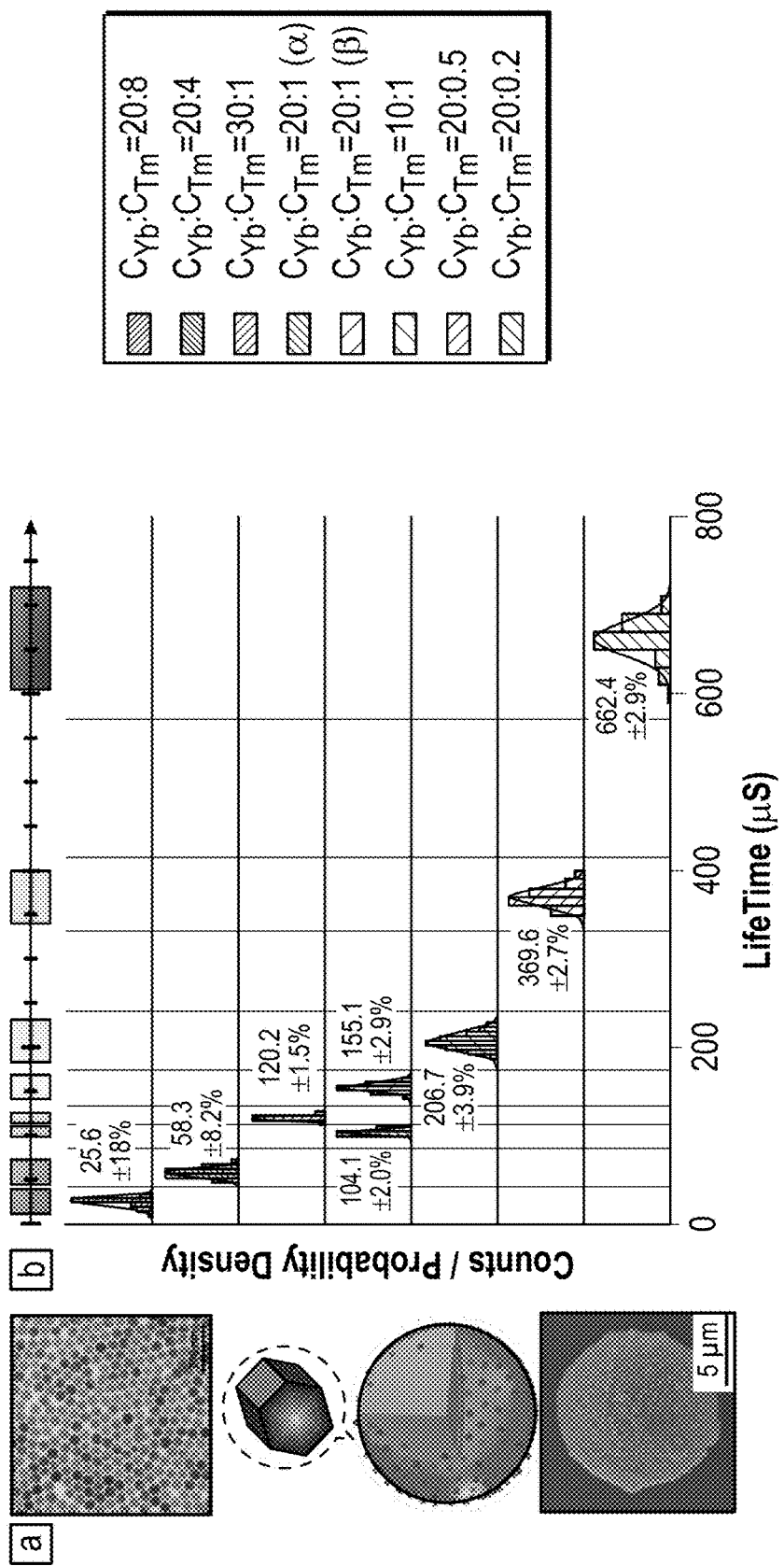
FIG. 10 shows results for example τ-Dots encoded populations of microspheres as the multiplexing suspension arrays carrying the unique lifetime codes: (a) The synthesized monodispersed Tm upconversion nanocrystals (top TEM image) can be embedded onto the microsphere shell (bottom SEM image). (b) The mechanism of upconversion energy transfer, by adjusting the co-dopant concentration of sensitizer-activator, can generate 8 lifetime populations of microspheres at Tm blue-emission band. The numeral besides each histogram is the mean lifetime±the lifetime CV from Gaussian distribution fitting. The blocks in the axis above represent the lifetime resources (±3σ) occupied by each population, while the open spaces suggest more populations could be engineered. (c) The 2-D (intensity vs. lifetime) scattered plots show all lifetime pollutions independent to intensities of individual micro-carriers.
Figure 10:
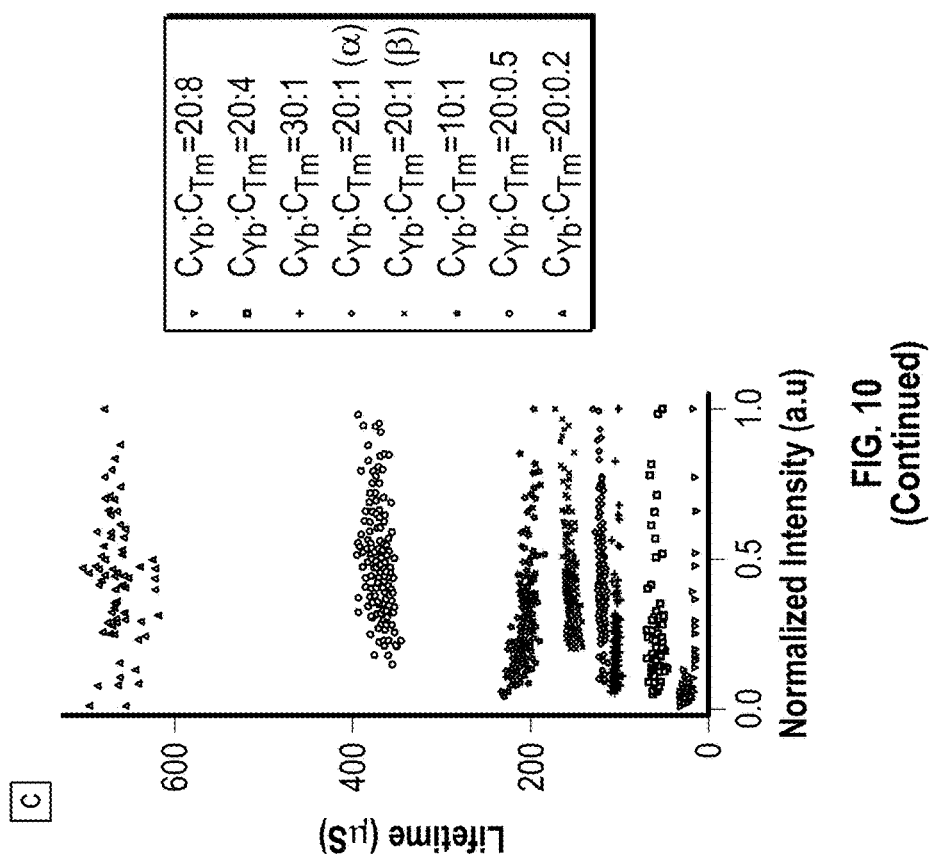

The τ-Dots also essentially remove the multiplexing restraints in known suspension arrays, where ensembles of microspheres are currently limited to only 100 colour and intensity coded channels (10 intensity levels at two colour emission bands). Shown in FIG. 10 is a new matrix of lifetime-coded microspheres created by absorbing the as-prepared nanocrystals discussed previously onto the shell of porous polystyrene microspheres (FIG. 10*d*). Both the lifetime and intensity of individual microspheres have been recorded during rapidly scanning by the time-resolved scanning cytometry system. As shown in FIG. 10*b*, the emitter (Tm) variation within the range 0.2 mol %-8 mol % (with the sensitizer Yb fixed at 20 mol %) resulted in a remarkably large range of lifetimes from 25.6 μs to 662.4 μs in the blue band. Increasing the Yb concentration from 10 mol % to 30 mol % (for Tm fixed at 1 mol %) also significantly accelerated the blue emission decay from 206.7 μs to 120.2 μs. This reflects the fact that higher concentrations of emitters and/or sensitizers leads to smaller average distance between sensitizers and emitters, and enhanced energy transfer rate.

For the time-resolved confocal scanning microscopy a fibre-optic confocal microscope using a single-mode fiber 980 nm laser source (LE-LS-980-300-FCS, LEO Technology Ltd., Shenzhen, China) and an oil-immersion objective (100×, NA=1.4, Olympus) to focus the excitation light onto the sample slide was used. The luminescence signal from the sample was collected by the same objective, split from the excitation optical path through a dichroic mirror (ZT765dcspxrxt, Chroma). It further transmits a band-pass filter (FF02-475/50, Semrock) before being coupled into a multi-mode fibre (M24L01, Thorlabs), which was connected to a photo-counting avalanche photodiode (SPCM-AQRH-13-FC, PerkinElmer). To acquire confocal images, a piezo-scanning stage (Nanomax-TS, Thorlabs) was employed to move the specimen, and the luminescence decay curve after pulsed excitation represented in photo counts were recorded for each pixel. The scanning and data collection were performed via a multifunction data acquisition device (USB-6353, National Instruments). A fast fitting algorithm based on the successive integration method and linear regression was adopted to achieve high robustness for real-time extraction of lifetime parameters, instead of common nonlinear algorithms such as maximum likelihood fitting.

It was also found that cubic-phase crystals typically yield shorter lifetimes than the hexagonal-phase, owing to an increased level of crystal defects and internal quenching. By using this approach one can tune the lifetime of 1 Tm/20Yb (mol %/mol %) nanocrystals from 155.1 μs (in hexagonal phase) to 104.1 μs (in cubic phase). Interestingly, for each of these population groups, even though the intensity varies across two orders of magnitude (FIG. 10*c*), the lifetime coefficient of variation (CV) can be as low as 1.5% (at most 3.9% for most populations other than the two with shortest lifetimes, whose CVs are slightly larger due to small average values). These results show the lifetime codes are completely independent to intensity, therefore free of compensations, further representing an overwhelming advantage compared to known spectral-domain cytometry methods. The narrow CVs can be used to achieve at least eight completely separated lifetime channels in blue, and there is sufficient potential for ten or more channels in total in blue (noting the large gaps among the last three populations).

The purposely-engineered multiplexed τ-Dots carrying distinguishable lifetime codes can also be applied in the photonics area of high-capacity data storage and data security, on top of the currently available other optical dimensions of wavelength and polarization, as well as spatial dimensions.

Figure 11:
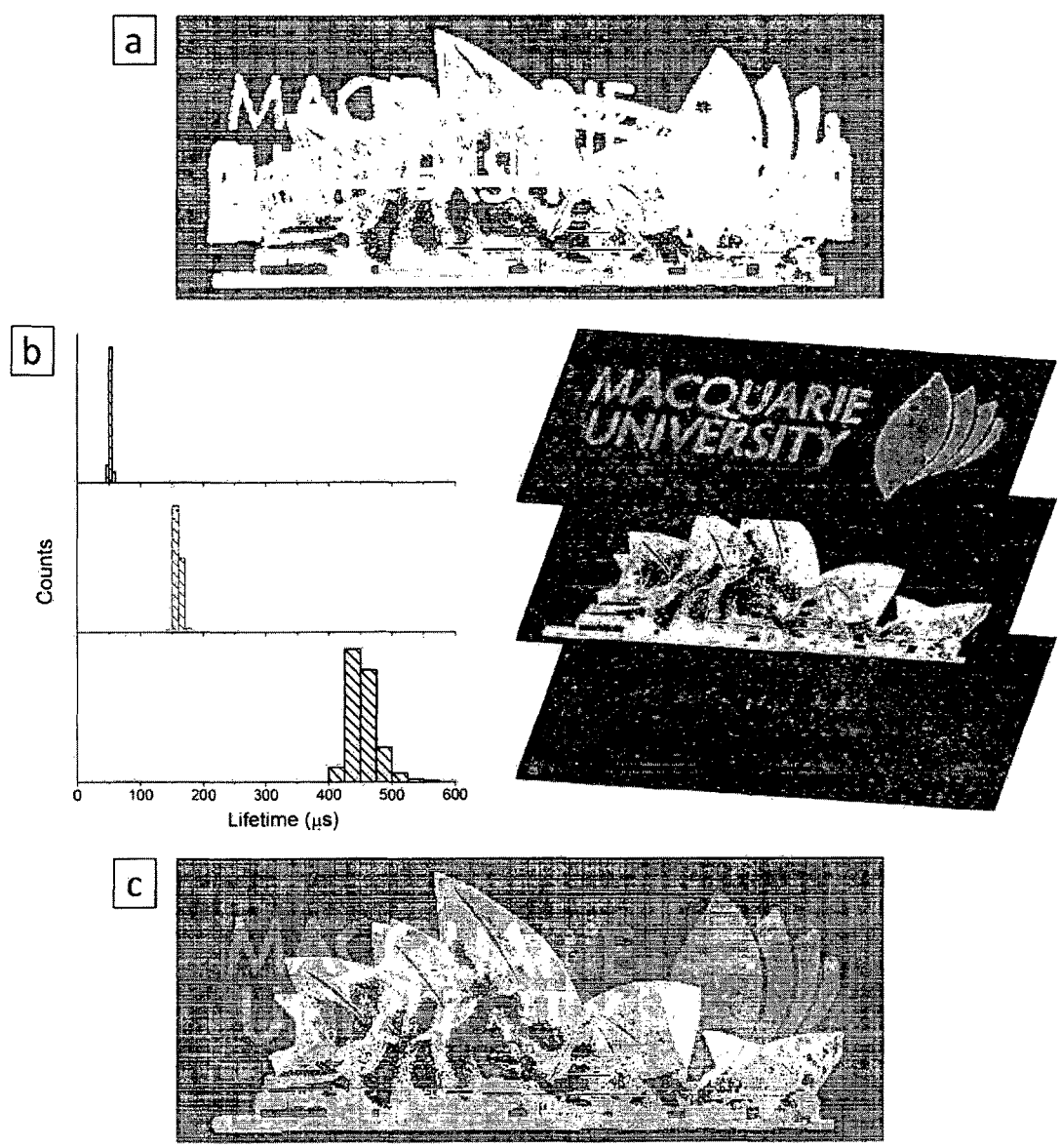
FIG. 11 shows an example application of lifetime-encoded document security and photonic data storage. Three overlapping patterns are printed with different Tm τ-Dots: ($C_{Tm}$:$C_{Yb}$) 4:20 for the "Macquarie University" logo; 1:20 for the Opera House image, and 0.5:20 for the Sydney Harbor Bridge image. While intensity-based luminescence imaging only gives a complex difficult to resolve picture (a), in contrast time-resolved scanning separates the patterns based on the lifetimes of every pixel (b), so that the genuine multiplexing information contained in the same overlapping space of document can be decoded (pseudocolour/scale used to map the luminescence lifetime for each pixel in c).

FIG. 11 illustrates a blended picture encompassing three overlapping pictures printed with τ-Dots of Tm:Yb ratios at 0.5:20, 1:20 and 4:20 (mol %:mol %), respectively. Although normal luminescent colour imaging cannot tell what is concealed in the blended picture (FIG. 11*a*), use of time-resolved scanning cytometry clearly decoded the blended image into three individual pictures/images since they exhibited distinct lifetimes of 48 μs, 155 μs and 450 μs (FIG. 11*b*). In one example, this demonstrates the application of a new type of document encryption using τ-Dots as security ink, so that only authorized persons who know the correct decoding rule of the luminescence lifetimes are able to obtain or retrieve genuine information or data, individual information or data, or component information or data, from a combined set of information or data or composite image.

For the security inks, the upconversion nanocrystals at low (0.5 mol %), medium (1 mol %) and high (4 mol %) Tm doping concentration (Yb concentration fixed at 20 mol %) in Tetrahydrofuran (1 mg/ml) were injected to commercial ink cartridges, respectively, to print the overlapping images of Macquarie Logo, Sydney Opera House and Sydney Harbour Bridge (dimensions: 40 mm×20 mm) onto a piece of normal paper by a commercial inkjet printer. After printing, the paper sample was mounted on a glass slide with the protection of cover slip, followed by image scanning by the time-resolved scanning cytometry system.

In another example, regular arrangement of such materials into sub-micron scale units provides a new solution for high-density data storage using lifetimes as digits. In particular, the presence/absence of one lifetime component can be used as one binary digit, so that one can achieve 8-bit capacity for each unit by simply using three types of lifetime-encoded nanocrystals. For both these examples, one outstanding virtue the method, device or system is that the complexity of the decoding system is not increased, because no additional light source, filter or detector is required.

Thus, there has been provided a new temporal domain approach for multiplexing. A new family of nano- or micro-tags, spheres, particles and/or carriers have been shown with separate lifetime identities independent to colours and intensities. These can be decoded without observable cross-talk. This allows libraries or databases of nano-/micro-probes to be developed, for example carrying more than 10,000 distinguishable codes (by combination of colour, intensity and lifetime), which dramatically increases the potential of fluorescence imaging or scanning as a powerful analytical technique able to cope with the complex challenges in various applications such as life sciences, medicine, high-density data storage and anti-forgery or authentication security.

Optional embodiments of the present invention may also be said to broadly consist in the parts, elements and features referred to or indicated herein, individually or collectively, in any or all combinations of two or more of the parts, elements or features, and wherein specific integers are mentioned herein which have known equivalents in the art to which the invention relates, such known equivalents are deemed to be incorporated herein as if individually set forth.

Although a preferred embodiment has been described in detail, it should be understood that many modifications, changes, substitutions or alterations will be apparent to those skilled in the art without departing from the scope of the present invention.

The invention claimed is:

1. A method for identifying a luminescent probe including one or more nanocrystals of a particular codopant material in a multiplex array, the method comprising:
    modifying a luminescence decay lifetime of a single emission color band of the luminescent probe while maintaining use of the particular codopant material, wherein the modified decay lifetime corresponds to one of a plurality of distinct decay lifetimes of the luminescent probe in the single emission color band; and
    identifying the luminescent probe by measuring the decay lifetime of the single emission color band, wherein the nanocrystals are doped with sensitizer and emitter ions from the rare earth group.

2. The method of claim 1, further including:
    engineering a plurality of luminescent probes to produce luminescence;
    measuring the decay lifetimes of the luminescence; and,
    time-resolving the luminescence decay to identify a type of luminescent probe.

3. The method of claim 2, wherein the time-resolved luminescence provides lifetime populations of different types of luminescent probe.

4. The method of claim 2, wherein the time-resolved luminescence decay provides one or more codes.

5. The method of claim 2, wherein the decay lifetimes of the luminescence are measured at distinct color bands.

6. The method of claim 5, wherein the distinct color bands are used to provide a library of time-domain based optical identities.

7. The method of claim 1, wherein the decay lifetimes is microsecond-to-millisecond decay lifetimes.

8. The method of claim 1, wherein luminescence of the luminescent probe is stimulated by UV and/or IR electromagnetic radiation.

9. The method of claim 1, wherein the decay lifetime of the luminescent probe has been altered by:
    using Luminescence Resonance Energy Transfer (LRET);
    changing respective concentrations of donor and acceptor;
    adding quencher dyes;
    using a metal matrix;
    altering the nanocrystals;
    adjusting a doping concentration of the nanocrystals;
    adjusting a different concentration of the sensitizer emitter ions;
    adjusting the size of the nanocrystals; and/or
    adjusting the crystal phase of the nanocrystals.

10. The method of claim 1, wherein the nanocrystals are rare-earth doped upconversion nanocrystals.

11. The method of claim 1, wherein the nanocrystals are doped with ytterbium sensitizer and erbium or thulium activators.

12. The method of claim 1, wherein the luminescent probe is a nano- or micro-tag, sphere, particle or carrier.

13. The method of claim 1, wherein measuring the decay lifetime of the luminescence is in addition to measuring the luminescence spectrum and luminescence intensity.

14. The method of claim 1, wherein the multiplex array is used for biological application, security application, or data storage application.

15. The method of claim 1, wherein engineering the luminescence decay lifetime includes manipulating the average distance between sensitizer and emitter ions.

16. A detection system for decoding a luminescent probe including one or more nanocrystals of a particular codopant material, the system comprising:
    a stimulator emitting infrared and/or UV radiation for exciting the luminescent probe to produce luminescence; and
    a photodetector for measuring a microsecond-to-millisecond decay lifetime of the luminescence of a single emission color band of the luminescent probe, the luminescence resulting from the excitation;
    wherein the luminescence decay lifetime is time-resolved through a successive integration method to identify the luminescent probe, wherein the luminescent decay lifetime is modifiable and corresponds to one of a plurality of distinct decay lifetimes of the luminescent probe in the single emission color band while maintaining use of the particular codopant material.

17. The system of claim 16, including a plurality of luminescent probes having different luminescent decay lifetimes.

18. The system of claim 16, wherein the luminescent probe is in solution/suspension, is part of a substrate, is part of a microsphere, or is a stain to label cells/biomolecules.

19. The system of claim 16, wherein the decay lifetime of the luminescent probe is between 25.6 µs and 662.4 µs.

* * * * *